United States Patent
Chen et al.

(10) Patent No.: US 10,317,499 B2
(45) Date of Patent: Jun. 11, 2019

(54) MRI WITH REPEATED K-T-SUB-SAMPLING AND ARTIFACT MINIMIZATION ALLOWING FOR FREE BREATHING ABDOMINAL MRI

(71) Applicant: Duke University, Durham, NC (US)

(72) Inventors: Nan-Kuei Chen, Cary, NC (US); Mei-Lan Chu, Durham, NC (US); Allen Song, Chapel Hill, NC (US)

(73) Assignee: Duke University, Durham, NC (US)

( * ) Notice: Subject to any disclaimer, the term of this patent is extended or adjusted under 35 U.S.C. 154(b) by 693 days.

(21) Appl. No.: 14/769,374

(22) PCT Filed: Mar. 25, 2014

(86) PCT No.: PCT/US2014/031711
§ 371 (c)(1),
(2) Date: Aug. 20, 2015

(87) PCT Pub. No.: WO2014/160701
PCT Pub. Date: Oct. 2, 2014

(65) Prior Publication Data
US 2016/0003928 A1    Jan. 7, 2016

Related U.S. Application Data

(60) Provisional application No. 61/805,633, filed on Mar. 27, 2013.

(51) Int. Cl.
*G01R 33/565* (2006.01)
*A61B 5/00* (2006.01)
(Continued)

(52) U.S. Cl.
CPC ...... *G01R 33/56509* (2013.01); *A61B 5/0042* (2013.01); *A61B 5/0044* (2013.01);
(Continued)

(58) Field of Classification Search
CPC .......... G01R 33/56509; G01R 33/5611; G01R 33/56308; G01R 33/5618; G01R 33/4822;
(Continued)

(56) References Cited

U.S. PATENT DOCUMENTS 6,144,200 A * 11/2000 Epstein .............. G01R 33/5615
324/306
6,404,196 B1 * 6/2002 Duerk ................. G01R 33/482
324/307

(Continued)

OTHER PUBLICATIONS

Application of Bootstrap Resampling in FMRI, http://archives.njit.edu/vol01/etd/2000s/2004/njit-etd2004-043/njit-etd2004-043.pdf, 2004.*
(Continued)

*Primary Examiner* — Patrick Assouad
*Assistant Examiner* — Demetrius R Pretlow
(74) *Attorney, Agent, or Firm* — Myers Bigel, P.A.

(57) ABSTRACT

Methods of processing MRI image data to reduce or eliminate motion-related artifacts in MRI images includes: electronically repeatedly acquiring sets of 2D or 3D k-space data of a target region of a subject using at least one MRI pulse sequence; electronically applying a bootstrapping procedure to produce a large number of images from the acquired k-space data; then electronically evaluating the images produced by the bootstrapping procedure; and electronically identifying an image with a minimal motion-related artifact level from the evaluation of the images produced by the bootstrapping procedure.

31 Claims, 12 Drawing Sheets

(51) Int. Cl.
| | |
|---|---|
| A61B 5/055 | (2006.01) |
| G01R 33/561 | (2006.01) |
| G01R 33/563 | (2006.01) |
| G01R 33/48 | (2006.01) |

(52) U.S. Cl.
CPC ............ *A61B 5/055* (2013.01); *A61B 5/7207* (2013.01); *G01R 33/4822* (2013.01); *G01R 33/5611* (2013.01); *G01R 33/5616* (2013.01); *G01R 33/5618* (2013.01); *G01R 33/56308* (2013.01); *A61B 2576/00* (2013.01)

(58) Field of Classification Search
CPC . G01R 33/5616; A61B 6/5264; A61B 5/7207; A61B 5/055; A61B 5/0042; A61B 5/0044; A61B 2576/00
USPC .......................................................... 324/309
See application file for complete search history.

(56) References Cited

U.S. PATENT DOCUMENTS

| | | | | |
|---|---|---|---|---|
| 2001/0027262 | A1 | 10/2001 | Mistretta et al. | |
| 2003/0102864 | A1* | 6/2003 | Welch | G01R 33/56509 324/307 |
| 2003/0117136 | A1* | 6/2003 | Wang | G01R 33/5676 324/306 |
| 2008/0054899 | A1* | 3/2008 | Aksoy | G01R 33/5611 324/307 |
| 2008/0116891 | A1* | 5/2008 | van der Kouwe | G01R 33/561 324/312 |
| 2008/0154115 | A1* | 6/2008 | Fuderer | G01R 33/5611 600/410 |
| 2009/0115794 | A1* | 5/2009 | Fukuta | G01R 33/561 345/581 |
| 2009/0284257 | A1* | 11/2009 | Bammer | G01R 33/56341 324/307 |
| 2010/0052677 | A1 | 3/2010 | Sueoka | |
| 2013/0063146 | A1 | 3/2013 | Riederer | |
| 2014/0210469 | A1* | 7/2014 | Cheng | G01R 33/56509 324/309 |
| 2015/0257675 | A1* | 9/2015 | Bottomley | G01R 33/34084 600/423 |
| 2015/0316635 | A1* | 11/2015 | Stehning | G01R 33/56341 324/307 |

OTHER PUBLICATIONS

Besl et al. "Method for registration of 3-D shapes", *IEEE Transactions on Pattern Analysis and Machine Intelligence*, vol. 14., No. 2, Feb. 1992, pp. 586-606.
Buehrer et al. "Array compression for MRI with large coil arrays", *Magnetic resonance in medicine, Official Journal of the Society of Magnetic Resonance in Medicine*, 2007;57(6):1131-1139.
Butts et al. "Interleaved echo planar imaging on a standard MRI system", *Magn Reson Med*. Jan. 1994; 31(1):67-72.
Chen et al. A robust multi-shot scan strategy for high-resolution diffusion weighted MRI enabled by multiplexed sensitivity-encoding (MUSE), *NeuroImage*, 2013;72:41-47.
Ehman et al. "Adaptive technique for high-definition MR imaging of moving structures" *Radiology* 1989; 173(1):255-263.
Eshed et al. "Claustrophobia and premature termination of magnetic resonance imaging examinations" *Journal of Magnetic Resonance Imaging*, JMRI 2007:26(2):401-404.

Forbes et al. "PROPELLER MRI: clinical testing of a novel technique for quantification and compensation of head motion", *Journal of Magnetic Resonance Imaging*, JMRI 2001;14(3):215-222.
International Preliminary Report on Patentability Corresponding to International Application No. PCT/US2014/031711; dated Oct. 8, 2015; 9 Pages.
Katz et al. "Anxiety and its determinants in patients undergoing magnetic resonance imaging", *Journal of behavior therapy and experimental psychiatry*, 1994:25(2):131-134.
Katznelson et al. "Prevalence of claustrophobia and magnetic resonance imaging after coronary artery bypass graft surgery", *Neuropsychiartic disease and treatment*, 2008;4(2):487-493.
Lukins et al. "A cognitive behavioral approach to preventing anxiety during magnetic resonance imaging", *Journal of behavior therapy and experimental psychiatry*, 1997;28(2):97-104.
Odille et al. "Generalized reconstruction by inversion of coupled systems (GRICS) applied to free-breathing MRI" *Magnetic resonance in medicine: Official Journal of the Society of Magnetic Resonance in Medicine / Society of Magnetic Resonance in Medicine*, 2008;60(1):146-157.
Oshio et al. "GRASE (Gradient- and spin-echo) imaging: a novel fast MRI technique", *Magnetic resonance in medicine, Official Journal of the Society of Magnetic Resonance in Medicine / Society of Magnetic Resonance in Medicine*, 1991:20(2):344-349.
Pipe JG, "Motion correction with PROPELLER MRI: application to head motion and free-breathing cardiac imaging", *Magnetic resonance in medicine: Official Journal of the Society of Magnetic Resonance in Medicine / Society of Magnetic Resonance in Medicine*, 1999;42(5):963-969.
Pruessmann et al. "SENSE: sensitivity encoding for fast MRI", *Magnetic resonance in medicine, Official Journal of the Society of Magnetic Resonance in Medicine / Society of Magnetic Resonance in Medicine*, 1999; 42(5):952-962.
Reddy et al. "An FFT-based technique for translation, rotation, and scale-invariant image registration", *IEEE transaction on image processing: a publication of the IEEE Signal Processing Society*, 1996;5(8):1266-1271.
Rohlfing et al. "Modeling liver motion and deformation during the respiratory cycle using intensity-based nonrigid registration of gated MR images", *Medical Physics*, 2004;31(3):427-432.
Samsonov et al. "POCSENSE: POCS-based reconstruction for sensitivity encoded magnetic resonance imaging" *Magnetic resonance in medicine, Official Journal of the Society of Magnetic Resonance in Medicine / Society of Magnetic Resonance in Medicine*, 2004;52(6):1397-1406.
Vasanawala et al. "Navigated abdominal T1-W MRI permits free-breathing image acquisition with less motion artifact", *Pediatric Radiology* 2010;40(3):340-344.
Wachtel et al. "Growth rates in pediatric diagnostic imaging and sedation" *Anesthesia and Analgesia*, 2009;108(5):1616-1621.
White et al. "Motion artifact correction in free-breathing abdominal MRI using overlapping partial samples to recover image deformations", *Magnetic resonance in medicine: Official Journal of the Society of Magnetic Resonance in Medicine / Society of Magnetic Resonance in Medicine* 2009;62(2):440-449.
International Search Report and Written Opinion for corresponding PCT Application No. PCT/US2014/031711, dated Sep. 24, 2014, 13 pages.
Jones et al., Confidence Mapping in Diffusion Tensor magnetic Resonance Imaging Tractography Using a Bootstrap Approach, Magnetic Resonance in Medicine, 2005, pp. 1143-1149, vol. 53.
Robson et al., Comprehensive Quantification of Signal-to-Noise Ration and g-Factor for Image-Based and k-Space-Based Parallel Imaging Reconstructions, Magnetic Resonance in Medicine, 2008, pp. 895-907, vol. 60.

\* cited by examiner

GSR=22.17%

GSR=9.73%

GSR=8.15%

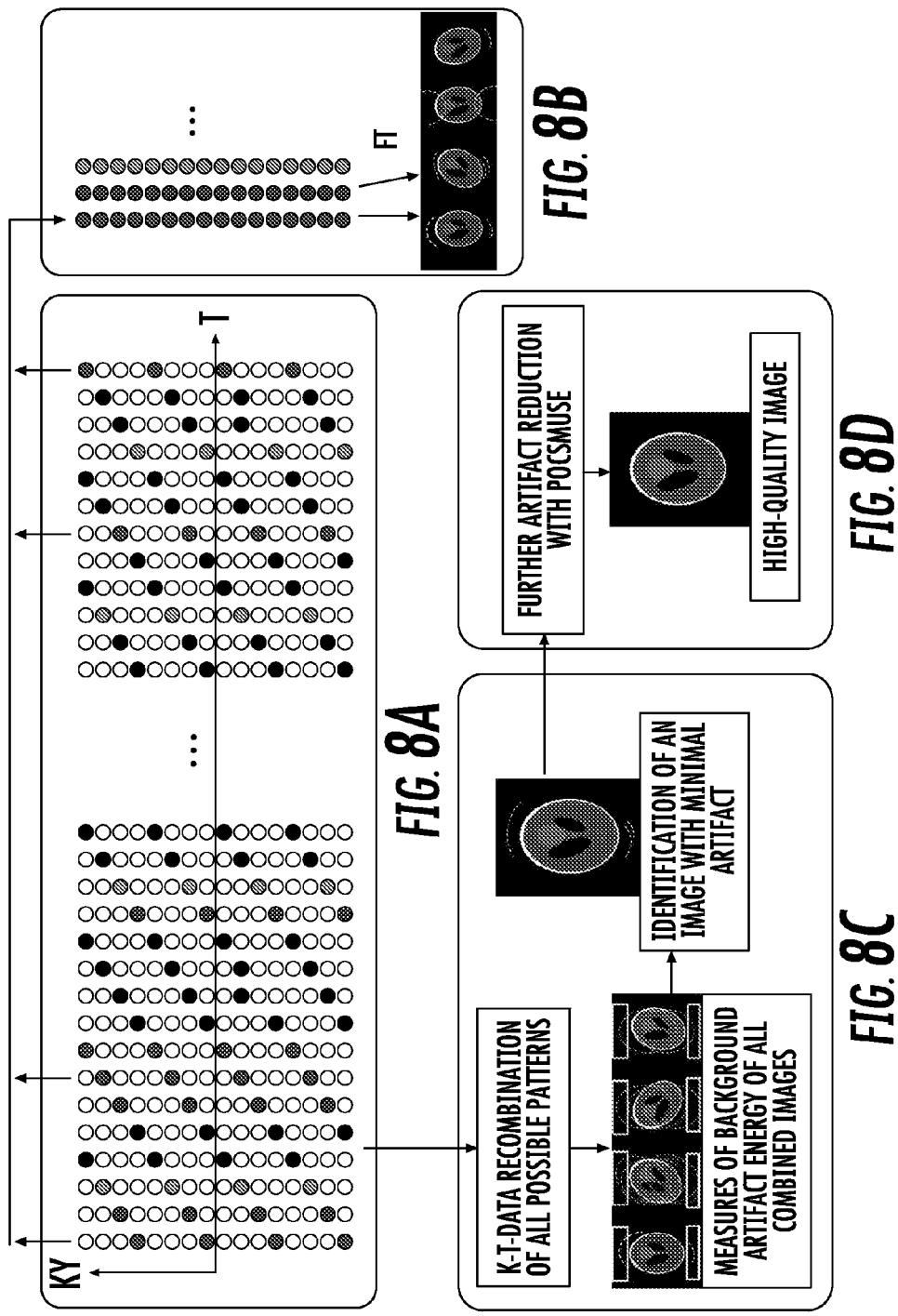

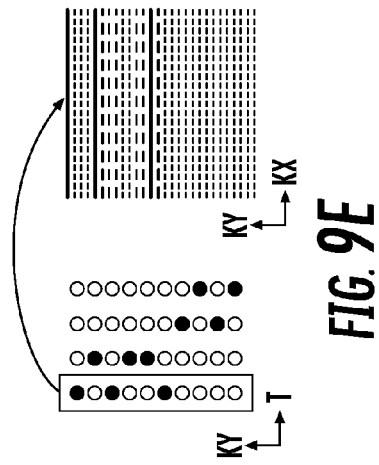
FIG. 9A
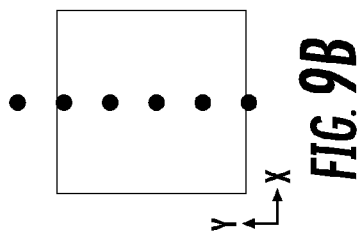
FIG. 9B
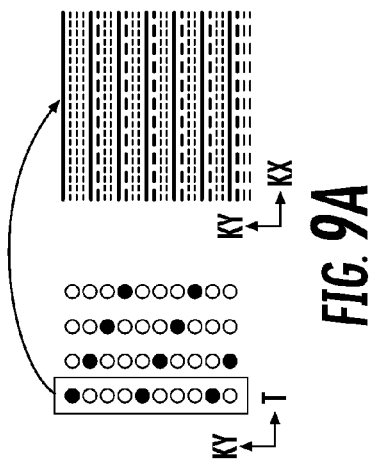
FIG. 9E
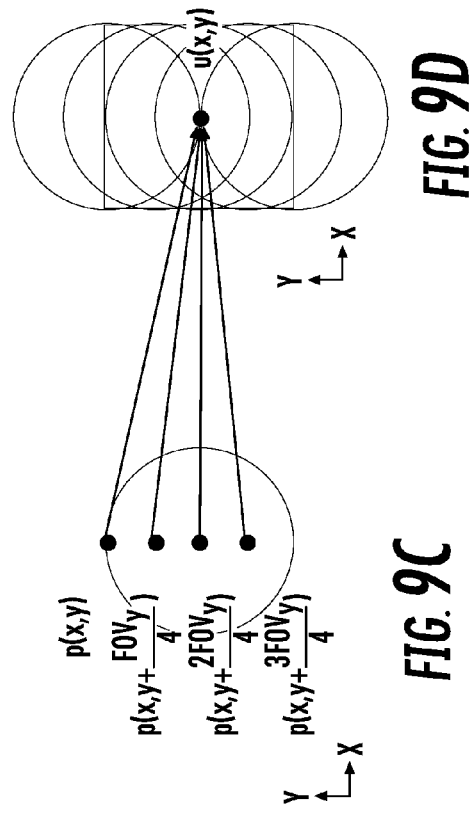
FIG. 9C
FIG. 9D
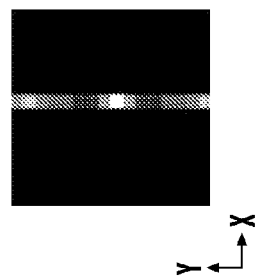
FIG. 9F

MRI WITH REPEATED K-T-SUB-SAMPLING AND ARTIFACT MINIMIZATION ALLOWING FOR FREE BREATHING ABDOMINAL MRI

RELATED APPLICATIONS

This application claims the benefit of and priority to U.S. Provisional Application Ser. No. 61/805,633 filed Mar. 27, 2013, the contents of which are hereby incorporated by reference as if recited in full herein.

BACKGROUND

Because MRI is highly susceptible to motion-induced artifacts, it has been challenging to generate high-quality MRI data in the presence of patients' continual and unpredicted motion. As a result, existing abdominal MRI protocols largely rely on either respiratory gating or breath-holding to reduce motion-related artifacts. However, the respiration-gated acquisitions have low scan efficiency, particularly when the subjects have irregular breathing. Breath-hold MRI has higher scan efficiency, but may not be feasible for seriously ill patients, and the temporal acquisition window is limited by the patient's breath holding capacity.

Free-breathing MRI is a preferred protocol for abdominal imaging, particularly in challenging patients who are unable to hold their breath for an extended period of time or have irregular respiratory rates. Several approaches have been developed to reduce motion-related artifacts in free-breathing abdominal MRI data using information derived from either navigator echoes (1,2) or the over-sampled central k-space data (e.g., PROPELLER) (3,4) However, it may be difficult to use signals of low spatial resolution to effectively remove artifacts resulting from nonlinear motion. To address this concern, a series of methods have been reported recently to better model the nonlinear deformation and improve the image quality of free-breathing abdominal MRI (5,6,7).

Motion artifact issues not only affects body MRI, but can also be a major concern in neuro-MRI scans for millions of patients from highly challenging populations (e.g., children, seriously ill patients, and tremor-dominant Parkinson's patients) who currently need to rely on risky sedation or anesthesia procedures to complete lengthy neuro-MRI scans. For example: 1) a significant subset of pediatric subjects (40% of children 0-2 years of age, 75% of those 3-5 years, and 10% of those 6-17 years) need to be sedated or anesthetized in order to complete MRI procedures of 30-60 min (8); 2) Up to 37% of adult patients undergoing MRI may experience moderate to severe fear and anxiety (9), and 5 to 14% of adult patients cannot complete the MR examination in the absence of sedation or anesthesia because of claustrophobia (9-12). Existing motion artifact reduction methods, such as navigator-echo based methods and PROPELLER, may not always completely eliminate artifacts in challenging patients such as tremor-dominant Parkinson's patients.

In view of the above, there remains a need for motion-immune MRI methods where high-quality neuro and/or free-breathing abdominal MRI data can be obtained from challenging patient populations without requiring sedation or anesthesia procedures.

SUMMARY OF EMBODIMENTS OF THE INVENTION

Embodiments of the invention are directed to MRI data processing methods, circuits and systems that can produce free-breathing abdominal MRI data of high-quality.

The new methods and can be termed Repeated K-t-sub-sampling and Artifact-Minimization ("ReKAM") are capable of effectively reducing motion-related artifacts during a free-breathing abdominal MRI scan without relying on navigator echoes or mathematically modeling the image deformation. These methods can be generally applied to existing abdominal MRI protocols providing different clinically-required contrasts.

The ReKAM framework is compatible with a variety of pulse sequences, and generally applicable to Cartesian and non-Cartesian MRI data including irregular data sampling in Cartesian or non-Cartesian k-space.

In some particular embodiments, the image processing (ReKAM) framework can use one acquisition module and two reconstruction modules. For the acquisition module, multiple sets of segmented k space data are first acquired. Motion artifacts are then minimized by at least one, typically two, reconstruction module: 1) a bootstrapping module used to identify an image with the least artifact; and 2) a constrained reconstruction module.

The constrained reconstruction module can integrate projection onto convex set (POCS) and multiplexed sensitivity encoding (MUSE), which can be termed "POCSMUSE." The constrained reconstruction module can be applied to further remove residual artifact.

The POCSMUSE protocol used with ReKAM can be applied to both Cartesian and non-Cartesian MRI data. ReKAM can employ many different MRI pulse sequences including, but not limited to, pulse sequences for abdominal fast-spin-echo (FSE) anatomic scans and free-breathing abdominal DWI.

Some embodiments are directed to methods of processing MRI image data to reduce or eliminate motion-related artifacts in MRI images. The methods include: (a) electronically repeatedly acquiring sets of 2D or 3D k-space data of a target region of a subject using at least one MRI pulse sequence; (b) electronically applying a bootstrapping procedure to produce a large number of images from the acquired k-space data; then (c) electronically evaluating the images produced by the bootstrapping procedure; and (d) electronically identifying an image with a minimal motion-related artifact level from the evaluation of the images produced by the bootstrapping procedure.

The method can include, after the electronic identification, programmatically applying a constrained reconstruction algorithm to remove residual artifact in the identified image to thereby generate an MRI image with reduced residual motion-related artifacts.

The at least one MRI pulse sequence can have regular segmented k-space sampling.

The at least one MRI pulse sequence can include at least one of segmented echo-planar imaging (EPI), segmented fast spin-echo imaging (FSE), segmented gradient-echo and spin-echo (GRASE) imaging, in which all segments have the same number of $k_y$ lines and the same inter-$k_y$ distance in 2D imaging or the same number of $k_y$-$k_z$-planes and the same inter-$k_y$ distance in 3D imaging.

The at least one MRI pulse sequence can have an irregular segmented k-space sampling.

The at least one MRI pulse sequence can include segmented fast spin-echo imaging (FSE) in which all segments have different numbers of $k_y$ lines and different inter-$k_y$ distances in 2D imaging or different numbers of $k_y$-$k_z$-planes and different inter-$k_z$ distances in 3D imaging.

The at least one MRI pulse sequence can be configured to sample k-space in a non-sequential manner.

The at least one MRI pulse sequence can include either or both (a) modified spoiled gradient-echo imaging (SPGR) and (b) modified magnetization prepared rapid gradient echo (MP-RAGE) sequences, in which k-space sampling trajectories are modified from a sequential manner to a segmented manner.

The at least one MRI pulse sequence can be configured to sample k-space in a sequential manner.

The at least one MRI pulse sequence can include SPGR and/or MP-RAGE imaging sequences.

Other embodiments are directed to methods for generating high-resolution, free-breathing abdomen MRI images. The methods include: (a) electronically applying a bootstrapping procedure to produce a large number of images from acquired sets of 2D or 3D k-space data; then (b) electronically evaluating the images produced by the bootstrapping procedure; and (c) electronically identifying an image with a minimal motion-related artifact level from the evaluation of the images produced by the bootstrapping procedure.

The method may include, after the electronic identification, programmatically applying a constrained reconstruction algorithm to remove residual artifact in the identified image to thereby generate an MRI image with reduced residual motion-related artifacts.

The electronic application of the bootstrapping procedure can be carried out by: regrouping the acquired k-space data across repeated runs irrespective of subject position during a respective acquiring run and using (i) all possible or selected k-t-space regrouping patterns of all the k-t space data or (ii) all possible or selected patterns of a defined center portion of the k-t space data, to produce a large number of regrouped k-space data; to reconstruct images from all the regrouped k-space data with Fourier transform.

The automatic evaluation to identify the image with the minimal artifact level can be carried out by at least one of the following: (i) electronically measuring a ghost energy level in defined regions of interest (ROI) located in a background area provided that a low ghost energy level indicates a low artifact level in images obtained with non-sequential MRI pulse sequences used for the acquiring step; (ii) electronically measuring an entropy level of a whole image provided that a low entropy level indicates a low aliasing artifact level in images obtained with non-sequential MRI pulse sequences used for the acquiring step; or (iii) electronically measuring a blurring level of a whole image provided that a low blurring level indicates a low artifact level in images obtained with sequential pulse sequences that are used for the acquiring step.

The constrained reconstruction algorithm can be carried out using known RF coil sensitivity profiles of the RF coils used to acquire the k-space data to solve a full field-of-view (FOV) proton density source image without aliasing artifacts, jointly from all or at least two parts of k-space data segments, thereby assuming that the proton density source image remains consistent across multiple k-space data segments.

The full-FOV proton density source image can be reconstructed from the acquired k-space data and the known coil sensitivity profiles using at least one of the following: a direct matrix inversion suitable for MRI data obtained with regular k-space sampling and typical k-space segment trajectories; or projection onto convex sets (POCS) for MRI data obtained with irregular k-space sampling and irregular k-space segment trajectories.

The constrained reconstruction algorithm can be carried out using known RF coil sensitivity profiles of the RF coils used to acquire the k-space data. The constrained reconstruction can include: electronically estimating a first proton density source image; electronically calculating representations of the estimated proton density source image in all of the RF coils; electronically projecting experimentally acquired data to the estimated images in the corresponding RF coils to generate projected images; electronically integrating the projected images from all coils to form a new estimated proton density source image; and iteratively repeating the calculating, projecting and integrating steps until a new estimated proton density source image converges so that an absolute variation of an iteration falls below a predefined tolerance value.

The projection, where used, can be achieved by replacing certain $k_y$ lines of the k-space data of the estimated images with experimentally acquired signals.

The bootstrapping procedure can be carried out using one or more of the following to reduce computational demands: (i) electronically performing the bootstrapping procedure on only a central portion of the k-space data rather than full k-space data; (ii) electronically using embedded navigator echoes to identify and exclude data points which do not correspond to the same position from the bootstrapping procedure; (iii) electronically using non-MRI measures of patient position or movement and exclude data points which do not correspond to the same position from the bootstrapping procedure; or (iv) electronically using a multi-core CPU and/or GPU to perform parallel computation of the bootstrapping procedure.

A k-t-data regrouping scheme used in the bootstrapping procedure is not required to match a segmented k-space sampling scheme used in data acquisition of the k-space data.

The k-t data regrouping scheme used in bootstrapping procedure can be carried out by one of more of the following: a segmented k-space sampling scheme used in data acquisition; or further decomposition of the $k_y$ lines acquired from each segment into two or more bootstrapping units.

The method can be applied to free-breathing abdominal MRI, cardiac MRI, neuro-MRI and other anatomical regions susceptible to motion-related artifacts.

Still other embodiments are directed to MRI image generation systems with an image processing circuit. The circuit includes (a) a k-t space data acquisition module and (b) a bootstrapping procedure reconstruction module configured to regroup acquired k-space data from the k-t space data acquisition module across multiple sets of 2D and/or 3D k-space data with all or selected possible patterns of (i) an entire k space data matrix or (ii) only a center portion of the k space data matrix, to generate different images with different motion-aliasing or induced artifact levels from respective regrouped k-space data sets, then identify a high quality image with a lowest artifact level from the different generated images.

The system can also include a constrained reconstruction module that integrates projection onto convex set and multiplexed sensitivity encoding using the identified lowest artifact level image from the bootstrapping procedure reconstruction module.

The image processing circuit can be in communication with and/or at least partially on-board an MR Scanner system.

The constrained reconstruction module can be applied to both Cartesian and non-Cartesian MRI data obtained from free breathing fast-spin-echo cardiac and/or abdominal scans and/or free breathing cardiac and/or abdominal DWI scans.

The data acquisition module can employ between 4-6 scans to generate respective 4-6 2-D or 3-D k space data sets for the bootstrapping procedure.

Some embodiments are directed to an image processing circuit configured to electronically carry out any of the methods described above and/or herein.

Some embodiments are directed to an MR image processing system that includes at least one processor configured to carry out any of the methods described and/or claimed herein.

Yet other embodiments are directed to a data processing system with non-transitory computer readable storage medium having computer readable program code embodied in the medium. The computer-readable program code includes computer readable program code configured to carry out any of the methods described and/or claimed herein.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A illustrates data acquisition with accelerated 2D MRI (e.g., EPI). FIG. 1B illustrates artifact elimination based on data regrouping that can be achieved only when the information of subject position changes is known. FIG. 1C illustrates a k-t-bootstrapping procedure to eliminate motion-related artifacts even when the information of subject position changes is not available according to embodiments of the present invention.

FIG. 2A illustrates data acquisition with accelerated 3D MRI (e.g., 3D GRASE). FIG. 2B illustrates artifact elimination based on data regrouping which can be achieved only when the information of subject position changes is known. FIG. 2C illustrates a k-t-bootstrapping procedure to eliminate motion-related artifacts even when the information of subject position changes is not available according to embodiments of the present invention.

FIG. 4A illustrates a k-t-bootstrapping procedure is used to remove inter-k-t-segment motion and the produced image is examined against a pre-selected artifact level threshold. FIG. 4B shows that when the residual artifact resulting from intra-k-t-segment motion is higher than the pre-selected threshold, a series of images will be reconstructed from the output k-space data of k-t-bootstrapping procedure, corresponding to different levels of artifacts resulting from intra-k-t-segment motion, using parallel MRI methods (e.g., SENSE or POCSMUSE). FIG. 4C illustrates the automated identification of an image with the lowest level of artifact resulting from both inter-k-t-segment and intra-k-t-segment motions according to embodiments of the present invention.

FIG. 5A illustrates when the intra-TR motion is minimal, and the k-space data points within a TR correspond to the same subject position. FIG. 5B shows that motion-immune images can thus be produced by regrouping the k-t-space data, corresponding to the same position (e.g., red data points), using data in a TR as a unit. FIG. 5C shows that when the subject position changes within a TR period, then the data points within each TR need to be further decomposed before the data across multiple TRs can be regrouped to produce motion-immune images.

FIGS. 8A-8D are schematic diagrams of an exemplary 2D ReKAM technique. FIG. 8A illustrates that multiple sets of segmented k-space data are acquired with a segmented MRI pulse sequence (e.g. multi-shot FSE; multi-shot EPI). FIG. 8B illustrates that motion related artifacts can be largely reduced by appropriately regrouping the k-space data, if the information of subject position changes is available. FIG. 8C illustrates that a bootstrapping procedure in k-t-space can be used to produce an image with the lowest motion artifact level, even when the information of subject position changes is not available. FIG. 8D illustrates the use of a POCSMUSE constrained reconstruction algorithm that can be applied to further reduce residual motion related artifacts.

FIGS. 9A-9F are schematic illustrations of an example of regular sub-sampling in k-space (usually achieved with 4-shot segmented MRI) according to embodiments of the present invention. FIG. 9B illustrates a PSF corresponding to the first segment of FIG. 9A. FIG. 9C shows the true (unaliased) image-domain signals. FIG. 9D shows the aliased image-domain signal resulting from the k-space undersampling (e.g., the first segment only of FIG. 9A) with the aliasing pattern predictable by the PSF. FIG. 9E shows an example of irregular sub-sampling in k-space. FIG. 9F shows the complicated PSF corresponding to the first segment of FIG. 9E.

FIG. 11A shows uncorrected free-breathing data (slice 1, 2 and 3, in vertically aligned windows) have significant motion-related artifacts (with GSR>11%). FIG. 11B shows breath-holding data have higher image quality and lower artifact level (with GSR<9%). FIG. 11C shows that free-breathing data reconstructed by the ReKAM method have high quality and the lowest artifact level (with GSR<6.5%) according to embodiments of the present invention.

DETAILED DESCRIPTION

Figure 1A:
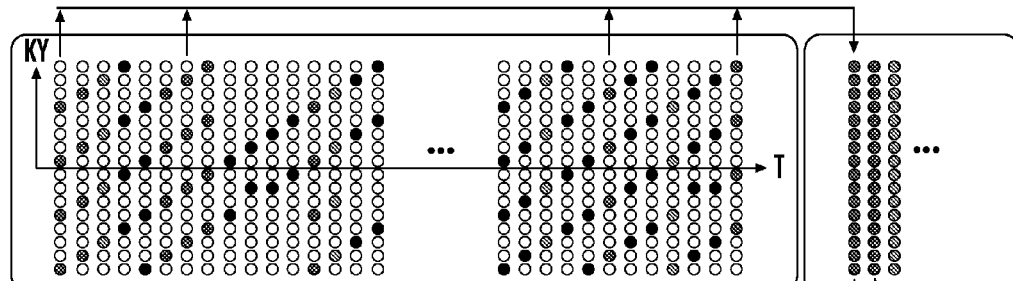
FIGS. 1A-1C are schematic diagrams of an exemplary 2D motion-immune MRI method according to embodiments of the present invention.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" or "MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5T/3.0T; Philips Medical Systems: Achieva 1.5T/3.0T; Integra 1.5T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above about 0.5 T, typically above 1.0T, and more typically between about 1.5T and 10T. Embodiments of the invention may be particularly suitable for 1.5T and 3.0T systems, or higher field systems such as future contemplated systems at 4.0T, 5.0T, 6.0T, 7T, 8T, 9T and the like.

The methods and systems can also be applied to animal MRI data acquired from animal MRI scanners.

The term "patient" refers to humans and animals.

The term "automatically" means that the operation can be substantially, and typically entirely, carried out without manual input, and is typically programmatically directed and/or carried out. The term "electronically" with respect to connections includes both wireless and wired connections between components.

The term "clinician" means physician, radiologist, physicist, or other medical personnel desiring to review medical data of a patient. The term "workstation" refers to a display and/or computer associated with a clinician.

The term "protocol" refers to an automated electronic algorithm and/or computer program with mathematical computations with defined rules for data interrogation, analysis and/or reconstruction that manipulates MRI image data.

The term "SENSE" refers to a sensitivity encoding protocol described by Pruessmann et al. Sense: sensitivity encoding for fast MRI. Magn Reson Med 42(5), 952-62 (1999), the contents of which are hereby incorporated by reference as if recited in full herein.

The term "high resolution" means that the achieved spatial-resolution is higher than that achieved with conventional (e.g., single-shot EPI pulse or multi-shot FSE, DWI) sequences. For example, a sub-millimeter spatial resolution which is an increase in resolution of 2x or more over conventional single shot EPI (e.g., 0.5 mm×0.5 mm, while the in-plane resolution achieved with conventional single-shot EPI is about 2 mm×2 mm).

Figure 11:
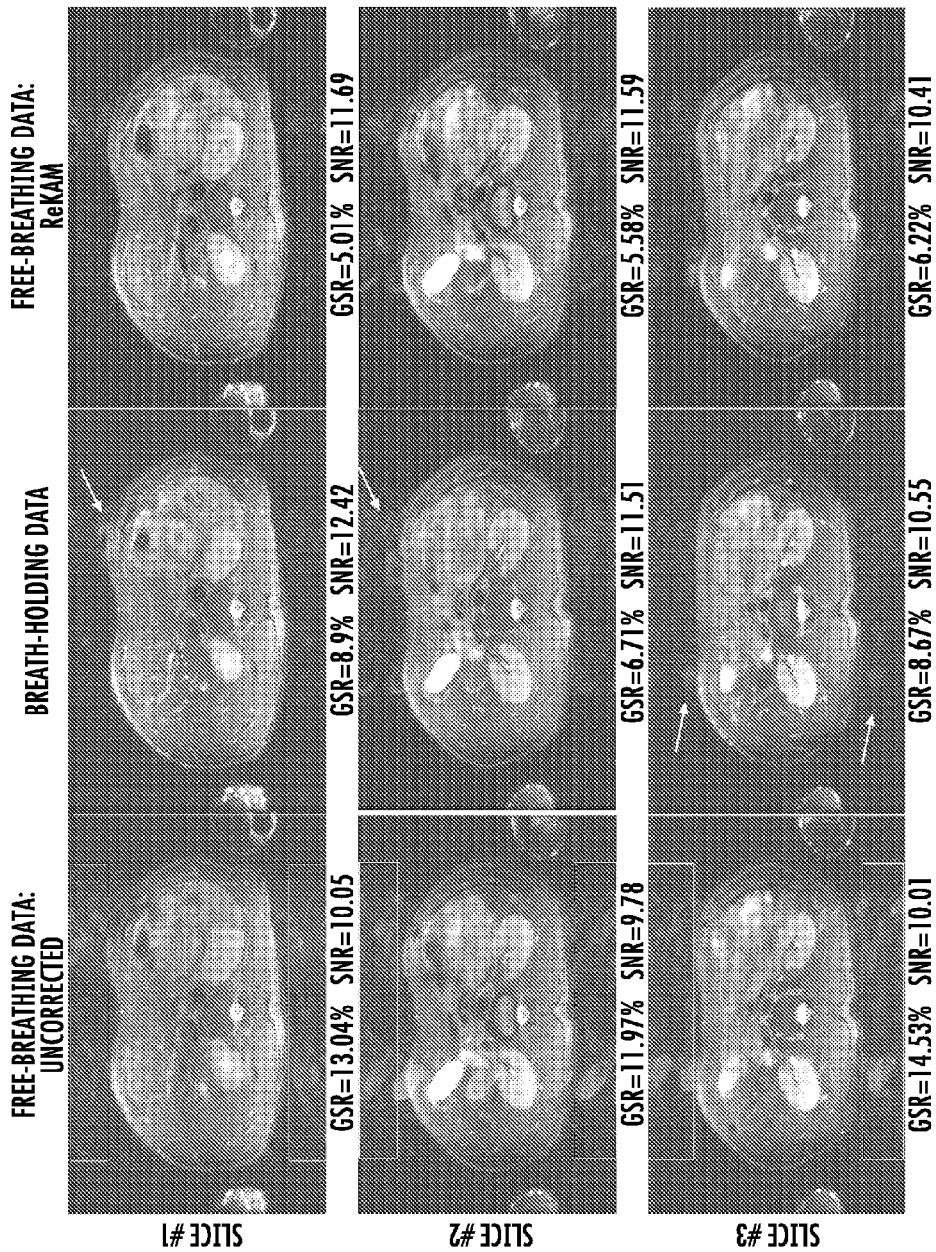
FIGS. 11A-11C are images of three selected slices acquired from a subject.

The term "high-quality" with respect to image quality refers to a low aliasing artifact level measured by a ghost-to-signal ratio ("GSR"). MR images can be considered motion-artifact and/or aliasing free if the ghost-to-signal ratio (GSR) is less than 10%. The GSR of motion-immune images can typically be between about 5% and about 6.22%. See, e.g., FIG. 11C. Stated differently, in some embodiments, the GSR in MRI data obtained with ReKAM reconstruction can be at least three times lower than that in uncorrected free breathing images and also better than breath-hold data (FIGS. 11A, 11B, respectively).

The term "motion-immune" means that the image processing is carried out so that the generated MRI image is motion-artifact free or that any motion-induced artifact(s) is reduced to a level that is clinically acceptable, even when the subject target anatomy moves during a scan associated with data acquisition (e.g., the GSR is less than about 6.25%).

The term "interleaved EPI" is well known in the field. See, e.g., Butts K, Riederer S J, Ehman R L, Thompson R M, Jack C R. Interleaved echo planar imaging on a standard MRI system. Magn Reson Med. 1994 January; 31(1):67-72.

The term "multi-shot interleaved MRI pulse sequences" refers to MRI pulse sequences associated with interleaved echo-planar imaging (EPI), interleaved fast spin-echo (FSE) imaging, interleaved spiral imaging, and other MRI pulse sequences that acquire multiple echo trains (e.g., multiple ky lines) after a single RF pulse excitation.

The term "inherently" means that the information (e.g., motion-induced phase errors) is derived directly from the actual (raw) MRI image data themselves without using external signals such as navigator echoes to adjust/correct image data to reduce or eliminate motion-induced aliasing artifacts.

The term "post-processing" with respect to the claimed methods means that the method is carried out after original MRI raw data in k-space of a respective subject is obtained.

The term "real-time" with respect to the boot strap reconstruction means that the k-space pattern reconstructions and associated Fourier transforms to generate resulting images can be carried out within about 0.1 second to about 3 minutes from when receiver coils receive MR image data to allow the boot strap reconstruction to control how long to continue k-t data acquisition and associated scan time of a patient to facilitate fast data throughput.

The term "large-scale intrascan motion" refers to significant patient movement, e.g., by about 1 voxel or greater than about 1 voxel during an MRI scan which generates aliasing artifacts in uncorrected image data.

The term "archived" refers to electronically stored patient image data that can be accessed and reconstructed into patient images/visualizations/renderings. The diagnostic task of a clinician such as a radiologist can vary patient to patient and, accordingly, so can the desired renderings or views of the medical images of the patient. In some visualization systems, a physician uses an interactive workstation that has a data retrieval interface that obtains the medical data for medical image renderings from electronic volume data sets to generate desired medical representations. Image visualizations using multi-dimensional MRI image data can be carried out using any suitable system such as, for example, PACS (Picture Archiving and Communication System). PACS is a system that receives images from the imaging modalities, stores the data in archives, and distributes the data to radiologists and clinicians for viewing.

The term "reconstruction" is used broadly to refer to original or post-image data acquisition and storage and subsequent construction of MRI image slices or MRI images of an image data set.

The term "bootstrapping procedure" refers to regrouping acquired k-space data across multiple sets of 2D and/or 3D k-space data with all or selected possible patterns of (i) an entire k space data matrix or (ii) a defined sub-portion of the data matrix, e.g., a center portion of the k space data matrix, to generate different images with different motion-aliasing or induced artifact levels from respective regrouped k-space data sets. The "selected possible patterns" may be selected based on non-MRI measures (e.g., belly belt based measurement of respiratory cycles) and k-space data points that obviously do not correspond to the same position can be excluded from the bootstrapping.

The term "constrained reconstruction algorithm" refers to a defined programmatic protocol that integrates multiplexed sensitivity encoding and projection onto convex data sets. It is also noted, for clarity, that while certain of the figures are described as "color" or "color-coded", to comply with filing rules, black and white copies or grey scale versions of these images may be used in support of the application.

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

The motion-artifact resistant clinical MRI methods can be described as having: 1) an acquisition module where k-space data is acquired using a defined MRI pulse sequence, e.g., with accelerated imaging comprising a fast imaging pulse sequence that can be used to rapidly and repeatedly acquire subsets of k-t-space data corresponding to different subject positions; and 2) at least one reconstruction module where reconstruction is based on k space-bootstrapping; an optional additional reconstruction module comprising the POCSMUSE procedure, may be used to further suppress residual artifacts in images obtained from the first reconstruction module. These modules can be provided as more than two modules or combined into a single module with the noted functional capability.

The at least one reconstruction module can be configured as a post-signal acquisition module or modules.

Examples of suitable pulse sequences include, but are not limited to, echo-planar imaging (EPI); fast spin-echo (FSE) imaging; gradient-echo and spin-echo imaging or GRASE (13), of different numbers of echo train lengths and segments.

Multiple images can be generated from the acquired k-space data using all or substantially all possible k-t data grouping patterns (i.e., bootstrapping in k-t-space, or k-t-bootstrapping). Motion-resistant (e.g., motion-artifact immune) images corresponding to multiple subject positions are then identified automatically. Examples of procedures of minimizing and/or eliminating motion artifacts in 2D and 3D MRI are described further below.

Figures 1B, 1C:
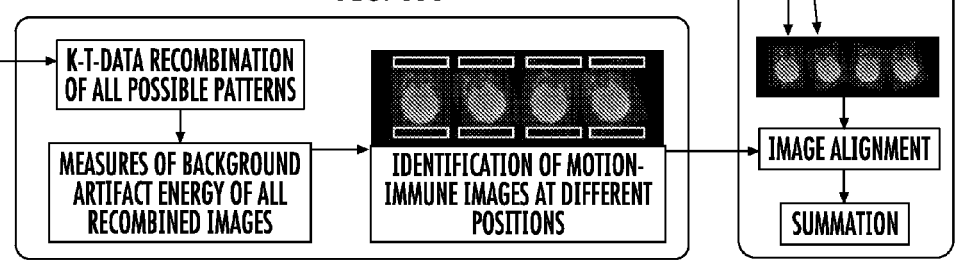

Turning now to the figures, FIGS. 1A-1C illustrate a 2-D example. A k-space data acquisition module is schematically illustrated in FIG. 1A, where k-t-space data are repeatedly acquired with accelerated 2D MRI (as shown, with EPI with a sub-sampling factor of 4). The solid and empty circles represent sampled and unsampled ky lines respectively, and the circles with the same color (e.g., red) correspond to approximately the same subject position while the position changes continually during scans. As illustrated in FIG. 1B, if the position information corresponding to every time point is known, then k-t-data corresponding to a particular position can be grouped to form an image with minimal artifacts (e.g., red k-space data points in FIG. 1B). However, the FIG. 1B artifact elimination based on data regrouping can be reliably achieved only when the information of subject position changes is known.

Practically, the patterns of intra-scan motion are unknown and unpredictable. Therefore, in the k-t-bootstrapping based reconstruction module (shown in FIG. 1C), a brute-force search strategy can be used to identify motion-immune images corresponding to different positions based on background artifact energy noise (an example is described below) to minimize, if not eliminate, motion-related artifacts even when the information of subject position changes is not known or available.

First, the acquired k-t-space sub-sampled data are regrouped using all possible data grouping patterns (i.e., k-t-bootstrapping), producing a series of images. Second, the background artifact energy of the produced images can be measured from in situ defined or pre-defined background ROIs (e.g., with the L2-norm method or other suitable method). Third, motion-immune images (i.e. images with the lowest background artifact energy in ROIs) corresponding to multiple positions can then be identified. Afterwards, the motion-immune images corresponding to different positions (e.g., red, blue and green k-data points) can be aligned, for example using the procedure outlined by Reddy et al (14), to minimize the blurring effect for subsequent combination.

An example of a suitable image alignment procedure is one developed by Reddy et al. and includes rotational and translational alignments. The value of the rotational alignment can be computed with the following steps. First (step 1), the magnitude components of two k-space data sets to be aligned can be computed. Then the magnitude k-space data points can be multiplied by a weighting factor that increases quadratically with the distance to the center of k-space, to enhance the high spatial-frequency information. Second, one of the weighted-magnitude-k-space data set produced by step 1 is used as a reference, and the other data set is rotated, at an angle between 0 to $2\pi$. Third, the 2D correlation coefficient between the reference and the rotated (weighted-magnitude-k-space) data sets produced by step 2 can be calculated, for assessing the similarity between these two data sets. Step 4), steps 2 and 3 can be repeated for different rotational angles. The angle corresponding to the largest 2D correlation coefficient represents the value to rotationally align the two original data sets. The value of the translational alignment can be computed with the following steps: 1) the cross-power spectrum of two images to be alignment is calculated; 2) by taking the inverse Fourier transform of the cross-power spectrum, an impulse response is generated; and 3) the amount of translational motion between two original images can be identified from the generated impulse response, where a non-zero value exists only at a location corresponding to the translational motion between two input images.

Figure 2A:
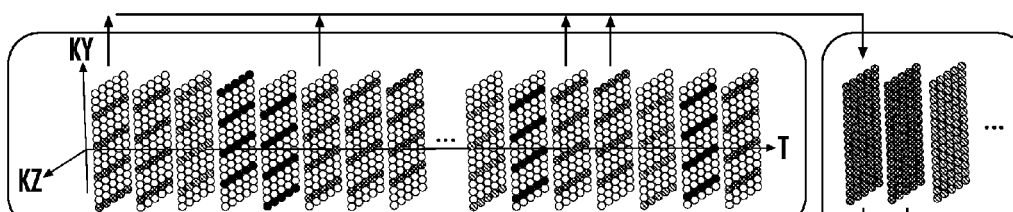
FIGS. 2A-2C are schematic diagrams of an exemplary 3D motion-immune MRI method.
Figures 2B, 2C:
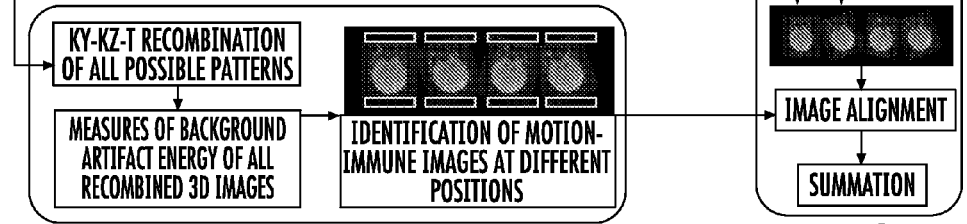

The method described above with respect to FIGS. 1A-1C can be directly extended to minimize (if not eliminate) artifacts induced by both in-plane and through-plane motion in 3D imaging, as illustrated by FIGS. 2A-2C with 3D GRASE acquisition as an example. Note that the methods described in this section can be directly applied to other 3D MRI pulse sequences, such as 3D FSE, for example.

In FIGS. 2A-2C, the data in ky-kz-t space are acquired by 3D GRASE with a sub-sampling factor of 4, using EPI echo train along the y-phase encoding direction and FSE echo train along the z-phase encoding direction. In 3D GRASE scans, the data acquired after a specific RF pulse excitation correspond to the same position (e.g., red circles in the sampling plane at a specific time). If the subject position at every TR time point is known, the sub-sampled ky-kz-t data of the same position (across multiple TRs) can be regrouped to form an artifact-free image as illustrated in FIG. 2B. However, this regrouping procedure may not be directly achieved since the patterns of subject motion are generally unknown and unpredictable. To address this issue, a reconstruction module exploiting the brute-force search strategy based on k-t-bootstrapping can be used to identify the motion-immune 3D images corresponding to different subject positions, as shown in FIG. 2C, which can minimize, if not eliminate, motion-related artifacts even when the information of subject position changes is not available.

The reconstruction methods can include the following steps. First, subsampled ky-kz-t data can be regrouped using all (or substantially all) possible grouping patterns (i.e., a bootstrapping procedure), producing a series of images with different artifact levels. Second, the background artifact energy can be measured from in situ defined or pre-defined ROIs of the produced images. Third, motion-immune images corresponding to multiple positions, free from motion-induced aliasing artifacts, can then be identified. Afterwards, the motion-immune images of different positions can be registered to reduce blurring effect for further combination, as appropriate.

The 3D image alignment procedure reported by Besl can be used (15) to address the rigid-body motion. However, other alignment protocols may also be used. Besl's method includes the following steps. First, the centroids of the to-be-aligned image $C_0$ and the reference $C_r$ are calculated using Equations 1 and 2.

$$\vec{C_r} = \frac{1}{N}\sum_{i=1}^{N}\vec{Q_i} \quad (1)$$

$$\vec{C_r} = \frac{1}{N}\sum_{i=1}^{N}\vec{Q_i} \quad (2)$$

where $\vec{P}_i[x_i y_i z_i]^T$ is the position vector of each pixel in the to-be-aligned image, $\vec{Q}_i$ is the position vector of the reference image, and N is the pixel number of the image. Second, the to-be-aligned image is shifted based on the distance between two centroids, to correct for the displacement between two images. Third, the cross-covariance matrix $\Sigma_0$ is calculated using Equation 3.

$$\Sigma_0 = \frac{1}{N}\sum_{i=1}^{N}\left[(\vec{P_i} - C_0)(\vec{Q_i} - C_r)^T\right] \quad (3)$$

Fourth, the singular value decomposition (SVD) of the cross-covariance matrix is calculated (Equation 4a), providing the information on the rotational motion between two images, quantified by a 3D rotation matrix R (Equation 4b).

$$\Sigma_0 = USV^T, \quad (4a)$$

$$R = V^T U^T \quad (4b)$$

Experimental Verification of 2D Motion-Artifact Free MRI

Figure 3A:
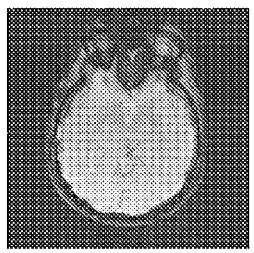
FIG. 3A illustrates a 2D motion-immune MRI reconstructed with ReKAM in the presence of continual head tremor according to embodiments of the present invention.
Figure 3B:
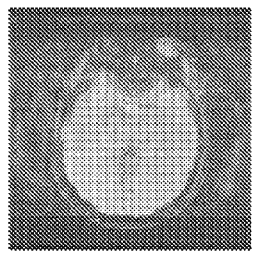
FIG. 3B illustrates 2D SPGR corrupted by continual head tremor: the display level is adjusted to show the artifacts in the background.
Figure 3C:
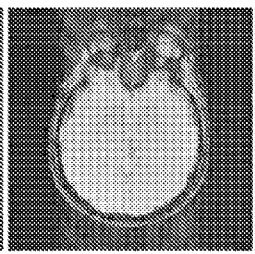
FIG. 3C is a temporally averaged image of the acquired k-t-space data using the scheme shown in FIGS. 1A-1C: the display level is the same as that in b, according to embodiments of the present invention.
Figure 3D:
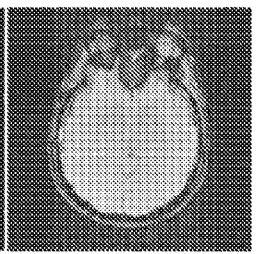
FIG. 3D is the motion-immune MRI shown in 3A with the display level the same as in 3B and 3C.

The 2D MRI procedure has been evaluated with human brain MRI studies performed on a 3 Tesla scanner to determine if the procedure successfully produces MRI images substantially (or totally) free from in-plane motion induced artifacts. The healthy participants were asked to have continual head tremor (at ~3 Hz) during i) a conventional T2*-weighted SPGR scan (scan time=10 sec) and ii) a repeated k-t-sub-sampling scheme (64 repetitions of T2*-weighted EPI with a sub-sampling factor of 8: total scan time=10 sec). The SPGR data were reconstructed with 2D FFT, and the repeated k-t-subsampled data were processed with either a direct 2D FT of temporally-averaged data (as for regular segmented EPI reconstruction) or the k-t-bootstrapping based reconstruction module (FIG. 1c). FIG. 3A shows the artifact-free image generated by the invented method, in the presence of continual head tremor. The conventional 2D SPGR, segmented EPI reconstruction of the acquired EPI k-t-space data, and the images reconstructed with the invented procedure are shown in FIGS. 3B, 3C, and 3D, respectively, with the display level elevated to better visualize the background artifacts. It can be seen that the SPGR image (3b) is severely corrupted by motion artifacts, with a ghost-to-signal ratio (GSR)>22%. The segmented EPI reconstruction of the temporally-averaged EPI data produces an image with a lower artifact level (with GSR=9.73%: FIG. 3C). Among these images, the image reconstructed with the new procedure using k-t bootstrapping as described in the instant application has the lowest artifact level (with GSR=8.15%: FIG. 3D), demonstrating the effectiveness of the developed motion-immune MRI technique for neuro imaging.

Figure 3E:
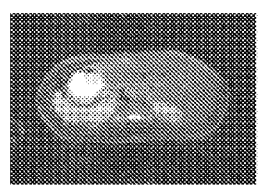
FIGS. 3E-3G are free-breathing abdominal images reconstructed from a single slice of free breathing FSE data with the ReKAM method according to embodiments of the present invention.
Figure 3F:
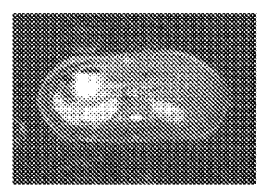
Figure 3G:
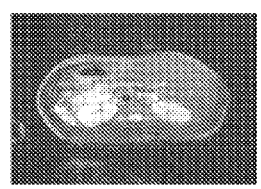
Figure 3H:
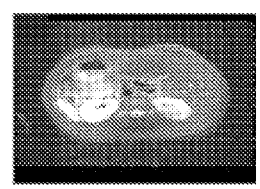
FIG. 3H is a respiration-gated scan of a single slice.

T2-weighted free-breathing body MRI studies were performed on a 3 Tesla scanner with a FSE sequence (with echo train length 48). Respiration-gated FSE data were also acquired for comparison. FIGS. 3E to 3G show three selected images reconstructed from a single slice of free-breathing FSE data using the k-t-bootstrapping method. It can be seen that the images from different anatomical positions were acquired from a single slice scan due to abdominal motion. As compared with the respiration-gated scan of a single slice (FIG. 3H), the integration of a free-breathing scan and the k-t-bootstrapping reconstruction provides images with similar quality but with greater scan efficiency. In addition to respiratory motion, cardiac motion may also result in motion-related artifacts in body MRI. It has been challenging to simultaneously remove both respiratory and cardiac motion related artifacts using existing methods. Using the proposed k-t-bootstrapping methods, it is feasible to eliminate artifacts resulting from both cardiac and respiratory motion in body MRI.

FIG. 3A illustrates 2D motion-immune MRI in the presence of continual head tremor. FIG. 3B illustrates a 2D SPGR corrupted by continual head tremor, the display level is adjusted to show the artifacts in the background. FIG. 3C shows a temporally averaged image of the acquired k-t-space data using the scheme shown in FIG. 1A. The display level is the same as that in FIG. 3B. FIG. 3D shows the motion-immune MRI shown with the display level the same as in FIGS. 3B and 3C.

Correction for Intra-TR Motion

The methods described above with respect to FIGS. 1A-C and 2A-C can be used to effectively remove artifacts resulting from changes of subject positions across multiple TRs (i.e., across different RF pulse excitations) assuming that the subject position remains the same within a TR.

In cases where the data acquisition window within each TR is long (e.g., in 3D GRASE with a long FSE echo train length), it is possible that the intra-TR motion is pronounced, resulting in blurring artifacts even after using the k-t-bootstrapping method described above. The artifacts resulting from intra-TR motion can be reduced with additional processing such as those discussed further below.

Integration of the k-t-Bootstrapping Method and Parallel Imaging

Figure 4A:
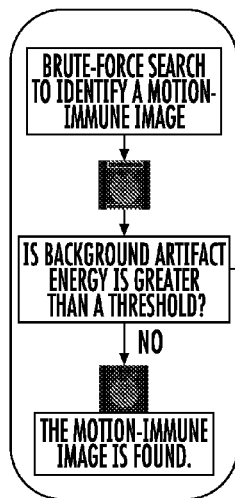
FIGS. 4A-4C illustrate a method for reduction and/or elimination of artifacts resulting from both inter-k-t-segment motion (i.e., among different TRs) and intra-k-t-segment motion (i.e., within a single TR) according to embodiments of the present invention.
Figure 4B:
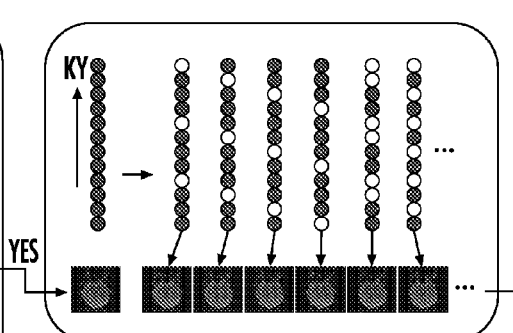

The intra-TR motion induced artifacts can be addressed by a procedure that integrates parallel imaging techniques, such as the sensitivity encoding (SENSE) (16), and the k-t-bootstrapping method. The integrated method is schematically illustrated with FIGS. 4A-4C. First, if the background artifact energy level of the k-t-bootstrapping produced image is lower than a predefined artifact-level threshold, then the k-t-bootstrapping produced image is determined to be motion-immune (FIG. 4A). Second, if the background artifact energy level of the k-t-bootstrapping produced image is higher than a predefined threshold due to pronounced intra-TR motion, then portions of the k-t-bootstrapping produced k-space data will be zero-filled and replaced by the values calculated from the remaining data points with the either POCSMUSE or SENSE method (FIG. 4B). When the intra-TR motion corrupted k-data points are zero-filled and replaced with the values calculated from un-corrupted data using the POCSMUSE or SENSE method, the motion-related artifacts can be further reduced. Depending on the number of receiver RF coils used for the k-space data acquisition, several different patterns of k-data zero-filling (i.e., the empty circles in FIG. 4B) can be performed, and the motion-immune image with the lowest background artifact energy level can be automatically identified (FIG. 4C).

Figure 4C:
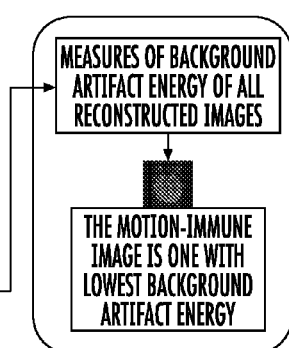

FIGS. 4A-4C illustrate further reduction (e.g., elimination) of artifacts resulting from both inter-k-t-segment motion (i.e., among different TRs) and intra-k-t-segment motion (i.e., within a single TR): FIG. 4A illustrates that the k-t-bootstrapping procedure is used to remove inter-k-t-segment motion and the produced image is examined against a pre-selected artifact level threshold. As shown in FIG. 4B, when the residual artifact resulting from intra-k-t-segment motion is higher than the pre-selected or pre-defined threshold, a series of images can be reconstructed from the output k-space data of the k-t-bootstrapping procedure, corresponding to different levels of artifacts resulting from intra-k-t-segment motion, using parallel MRI method (e.g., SENSE or POCSMUSE). FIG. 4C illustrates the identification of an image with the lowest level of artifact resulting from both inter-k-t-segment and intra-k-t-segment motions.

Reduction/Elimination of Image Blurring by Flexible Recombination Patterns

Figures 5A, 5B:
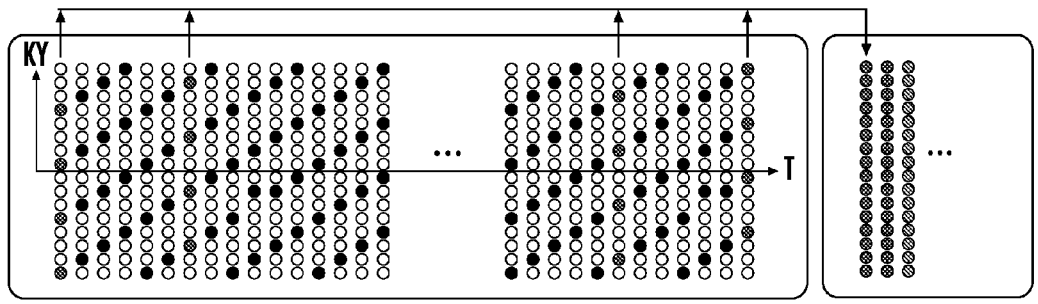
FIGS. 5A-5C schematically illustrate a 2D motion-immune MRI method according to embodiments of the present invention.
Figures 5C, 5D:
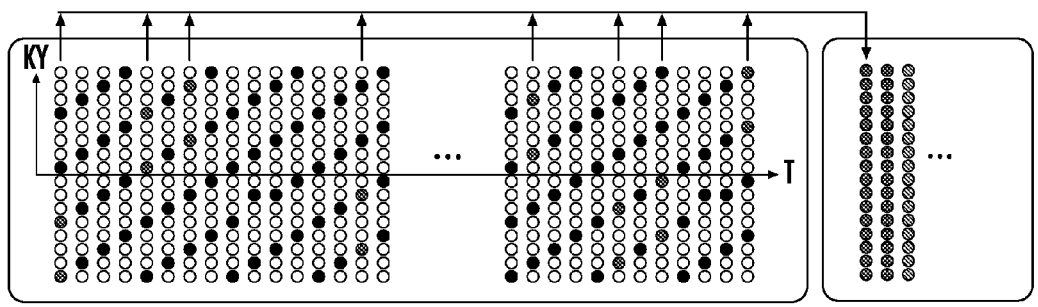
FIG. 5D shows that in the presence of intra-TR motion, the k-t-data regrouping patterns may thus be different from the sub-sampling patterns used for data acquisition.

The bootstrapping procedure described with respect to FIGS. 4A-4C, may be modified to further reduce the artifacts resulting from intra-TR motion. As illustrated in FIGS. 5A and 5B, when the intra-TR motion is insignificant, the k-space data points within a certain TR period correspond to the same subject position, and motion-immune images can be produced by performing the k-t-bootstrapping procedure (e.g., as discussed above with respect to FIGS. 1A-1C, 2A-2C) using data in a TR as a unit. In contrast, as illustrated in FIG. 5C, if the subject position changes within each TR, then the data points within each TR can be further decomposed before the data across multiple TRs can be regrouped to produce motion-immune images. As shown in FIG. 5D, for scans with pronounced intra-TR motion, the k-t-data regrouping patterns may be different from the sub-sampling patterns used in data acquisition.

FIGS. 5A-D illustrate an exemplary 2D motion-immune MRI method. FIG. 5A illustrates that when the intra-TR motion is minimal, the k-space data points within a TR correspond to the same subject position. FIG. 5B illustrates that motion-immune images can thus be produced by regrouping the k-t-space data, corresponding to the same position (e.g., red data points), using data in a TR as a unit. FIG. 5C illustrates that when the subject position changes within a TR period, then the data points within each TR can be further decomposed before the data across multiple TRs can be regrouped to produce motion-immune images. FIG. 5D shows that in the presence of intra-TR motion, the k-t-data regrouping patterns may thus be different from the sub-sampling patterns used for data acquisition.

Reduction of Computation Time of k-t-Bootstrapping Reconstruction

The computation cost for k-t-bootstrapping can increase with the number of TR time points, the number of sub-sampling factor, and the number of RF coils. Thus, in some embodiments, the reconstruction module can employ a reconstruction pipeline with relatively low computation time, even for MRI scans with a large number of TR and a high sub-sampling factor. Three different exemplary approaches to reduce the computation time of k-t-bootstrapping reconstruction are discussed below. However, it is contemplated that other protocols or methods may be used as an alternative to or in combination with these examples.

Acceleration of Reconstruction by Graphics Processing Unit (GPU)

Parallel structure in GPU can be used to lower the computation time. Note that the k-t-bootstrapping procedure can be decomposed into multiple, parallel processing units that can be independently (concurrently) performed. Therefore, these processes can be performed using the parallel computational units of GPU. It is expected that the computational time can be reduced by >10 fold using GPU based parallel computation.

Figure 6:
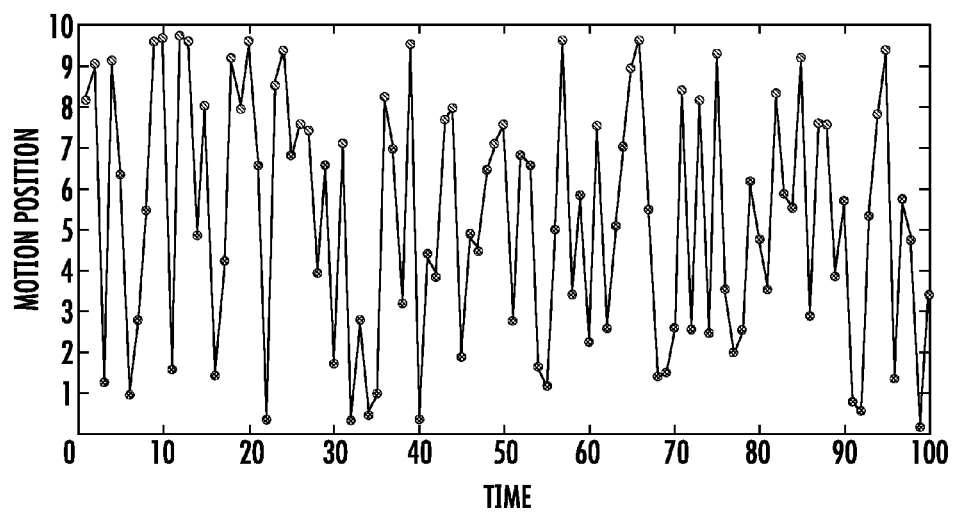
FIG. 6 is a graph illustrating that motion-based position over time that can be measured using position change information to reduce computation time/cost of a k-t-bootstrapping procedure using subject position change information derived from non-MRI measurements according to embodiments of the present invention.

Reduction of Computation Cost Using Additional Information from Non-MRI Measurements The unknown intra-scan motion can be estimated by using external non-MRI measurement. In this case, the brute-force search range and thus the k-t-bootstrapping computation cost can be reduced significantly by excluding k-t-data points that correspond to very different subject positions determined by external non-MRI modalities. For example, for brain imaging, the head motion can be recorded by one or more MR-compatible CMOS camera. As illustrated in FIG. 6, the acquired k-t-space data can be roughly classified based on the position information provided by the CMOS camera(s), and the k-t-bootstrapping can be performed only on data points corresponding to similar positions (e.g. circles with the same color) to reduce the computation cost. For body MR imaging, the electrocardiography (ECG) and a conformable, elastic stomach (e.g., belly) belt can be used to measure the cardiac and respiratory cycles, which can be used to reduce the search range and thus the computation cost of k-t-bootstrapping method for body MRI. FIG. 6 illustrates a reduction of the computation cost of the k-t-bootstrapping procedure using subject position change information derived from non-MRI measurements.

Acceleration of Data Reconstruction Using Array Compression Method

A large number of independent receiving coils, e.g., about 32 or more, are often used in MR imaging to take advantages of the recently developed parallel imaging methods. However, the computation cost for k-t-bootstrapping method increases with the number of RF coils, making it challenging to rapidly (immediately or in real-time) reconstruct images when the number of RF coils is very large (e.g., 32). To address this issue, the k-t-bootstrapping procedure can be integrated with an array-compression post-processing technique (17). First, the k-space data from n receiving coils can be linearly combined into composite k-space data of m virtual coils (n>m) based on noise minimization of specific ROI. Afterwards, the k-t-bootstrapping method can be applied on the data of virtual coils with reduced computational complexity.

Advantages of Real-Time k-t-Bootstrapping Based Image Reconstruction

Figure 7:
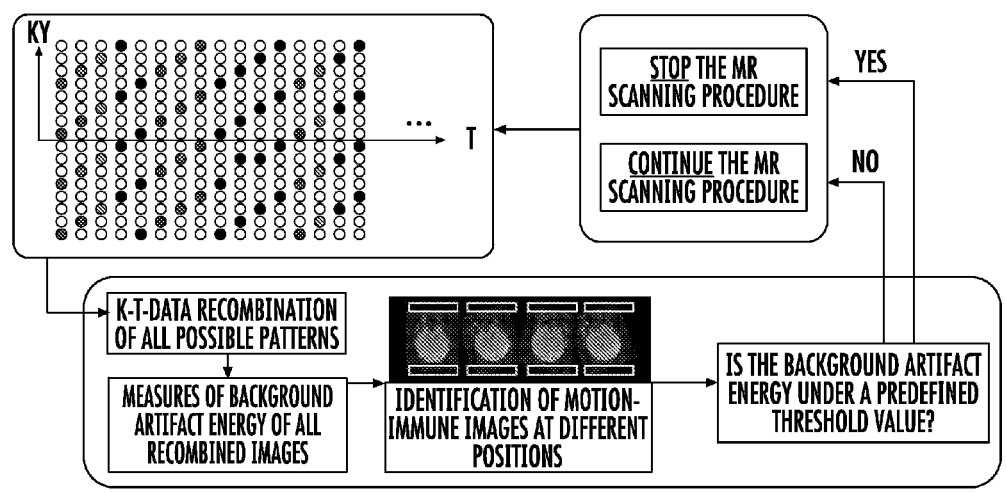
FIG. 7 is a schematic illustration of a method that provides control feedback to generate a motion-immune MRI data scan time with reduced scan time based on an integrated feedback control input with k-t-bootstrapping based reconstruction according to embodiments of the present invention.

Using computational reduction methods, it is contemplated that it will be feasible to perform k-t-bootstrapping with a low computation time, allowing real-time reconstruction of motion-immune (or highly resistant) and high-quality images. A real-time reconstruction is advantageous in clinical settings in many ways, such as the increase of data throughput. An important advantage of the real-time k-t-bootstrapping based image reconstruction is that the total MRI data acquisition time can potentially be shortened, through the proposed feedback system illustrated in FIG. 7. In the embodiment shown in FIG. 7, the MRI machine (Scanner) can acquire k-space data continuously, and the data can be immediately transmitted to a reconstruction module in one or more processors, such as in one or more client computers. The immediate transmission and reconstruction can be carried out rapidly, depending on bandwidth in the transmission path, typically in between about 0.1 seconds to about 3 minutes, such as between about 0.1 second and 2 minutes, more typically between about 0.1 seconds to about 30 seconds, from when the RF receiver coils detect the MRI data signal.

The motion-immune images can be identified by the k-t-bootstrapping method, and the quality of the reconstructed images can be measured by comparing the background artifact energy with a predefined threshold. When the artifact level is lower than the threshold, the at least one processor (e.g., client computer or a computer in communication with the at least one processor) can direct the MRI system to stop the MRI scanning. If the artifact level is higher than the threshold, the MRI system continues to scan until reaching either a pre-defined artifact level threshold or a pre-defined maximal scan duration. By using the optional feedback control system based on the real-time reconstruction, the amount of acquired data can be effectively controlled and the scan time can be potentially shortened.

Constrained Reconstruction

As discussed above, the image processing framework includes an acquisition module and at least one reconstruction module. For the acquisition, a segmented imaging pulse sequence (e.g., segmented echo-planar imaging (EPI), segmented fast spin-echo (FSE) imaging, or segmented gradient-echo and spin-echo imaging (GRASS) (13)) can be used to repeatedly acquire multiple sets of segmented k-t-space data regardless of the subject position. After repeated k-t-sampling, the artifact-minimization can be achieved by subsequently applying two reconstruction modules. First, as described above, multiple images can be reconstructed from the acquired data using all or substantially all possible k-t-data grouping patterns (i.e., bootstrapping in k-t-space), and high-quality images corresponding to one or multiple subject positions are then identified based on the reconstructed images using an automatic identification procedure such as measuring or evaluating the level of background artifact energy. Second, in some embodiments, a constrained reconstruction algorithm that integrates a projection onto a convex set (POCS) based parallel imaging (18) and multiplexed sensitivity encoding (MUSE) (19), ("POCSMUSE"), can be applied to the selected or identified image or images to further reduce and/or minimize the motion-induced aliasing artifacts. The ReKAM framework is compatible with a variety of pulse sequences, and generally applicable to irregular data sampling in Cartesian or non-Cartesian k-space. While the reconstruction is described using two modules, the functionality of the two reconstruction modules can be separated into more than two modules or combined into one integrated module.

FIGS. 8A-8D illustrate an example of the alternate reconstruction protocol. FIG. 8A illustrates that multiple sets of segmented k-space data can be acquired with a segmented MRI pulse sequence (e.g. multi-shot FSE; multi-shot EPI) irrespective of subject position. FIG. 8B illustrates that motion related artifacts can be largely reduced by appropriately regrouping the acquired k-t-space data, if the information of subject position changes is available. FIG. 8C illustrates that a bootstrapping procedure in k-t-space can be used to produce an image with the lowest motion artifact level, even when the information of subject position changes is not available. FIG. 8D illustrates further artifact reduction using the POCSMUSE constrained reconstruction algorithm which can be applied to the minimal artifact image to further reduce residual motion related artifacts.

In FIGS. 8A-8D, an example of a procedure is schematically illustrated to eliminating motion artifacts using a 4-shot segmented MRI pulse sequence (e.g., 4-shot FSE or 4-shot EPI) with a phased array receiving coil as an example. Note that the acquisition and/or reconstruction strategy can generally be applied to various pulse sequences with different echo train lengths and numbers of segments, as described below.

Acquisition Module: Repeated k-t-Sub-Sampling

The data acquisition module is shown in FIG. 8A, where the filled and open circles represent sampled and unsampled $k_y$ lines respectively, and the circles with the same color (e.g., red) correspond to approximately the same subject position while the position changes continually during scans. As illustrated in FIG. 8B, if the position information corresponding to every time point is known, then k-t-data corresponding to a particular position can be grouped to form an image with lesser amounts of artifact (e.g., red k-space data points in FIG. 8B).

Reconstruction Module 1: Bootstrapping in k-t-Space

Practically, the patterns of intra-scan motion are unknown and unpredictable. Therefore, in the bootstrapping based reconstruction module (shown in FIG. 8C), a brute-force search strategy can be used to identify images with the lowest artifact level using the following steps. First, the acquired k-t-space sub-sampled data are regrouped using all possible data grouping patterns (i.e. bootstrapping in k-t space), producing a large number of images. Second, the background artifact energy levels of the produced images are measured from pre-defined or in situ defined background ROIs with the L2-norm method. Third, the image with the lowest background artifact level in ROIs can be automatically, electronically and/or programmatically identified.

If the number of repetitions (i.e., the number of fully-sampled k-space sets) is large, then the bootstrapping reconstruction module can group the k-space data corresponding to the identical subject position and produce a high-quality and artifact-free image. However, it may be somewhat impractical to acquire data with a large number of repetitions during clinical scans. With a moderate number of repetitions (e.g., between about 3-10, typically between 4-5, repetitions), although the k-t-bootstrapping procedure can identify images with a lower artifact level, motion-induced aliasing artifact may still be present due to small residual inconsistencies within the k-t-space data sets. Therefore, in the secondary reconstruction module, e.g., a POCSMUSE module (FIG. 8D), a constrained reconstruction algorithm can be applied to further reduce motion-induced artifact (as will be described in see the section on Reconstruction module two (2)).

The reconstruction of all images generated by the bootstrapping procedure may be time consuming, particularly for a large number of repetitions. The computation cost can be significantly reduced by performing the bootstrapping reconstruction module on only a selected portion of k-space data, e.g., a central portion of the k-space data, typically about a 64×64 data set. Once a correct k-t-data regrouping pattern is identified, the k-space data of the original matrix size (e.g., 256×256) can be recombined accordingly, and then undergo the subsequent POCSMUSE reconstruction module. Other possible approaches for reducing the bootstrapping computation cost will be described in the Discussion section.

Reconstruction Module 2: POCSMUSE
SENSE Reconstruction of Undersampled Data Vs. Constrained Reconstruction of Fully Sampled Data Using the sensitivity encoding (SENSE) technique (16), a full-FOV image can be reconstructed from regularly under-sampled k-space data acquired with multi-channel coils. The SENSE algorithm can use 4× under-sampling scan, with the k-space scan trajectory and the corresponding point spread function (PSF) shown in FIGS. 9A (solid lines) and 9B, respectively. The aliased image reconstructed from the undersampled and zero-filled k-space data set can be represented by Equation 5, where $u_j$ represents aliased signal obtained by the j-th coil (j=1 to $N_c$; with $N_c$ being the total number of coils); $S_j$ is the coil sensitivity profile for the j-th coil; and p is the un-aliased full-FOV image to be reconstructed.

$$u_j(x, y) = \sum_{r=0}^{3} S_j\left(x, y + \frac{r \times FOV_y}{4}\right) p\left(x, y + \frac{r \times FOV_y}{4}\right) \quad (5)$$

With known coil sensitivity profiles, the full-FOV image p can be reconstructed by solving Equation 5 through matrix inversion.

Although the SENSE algorithm was originally designed for image reconstruction of undersampled k-space data, the mathematical framework can be extended to perform constrained reconstruction of fully sampled k-space data, comprising multiple segments of sub-sampled k-space data (e.g., solid and dashed $k_y$ lines in FIG. 9A). For example, Equation 5 can be modified to jointly incorporate all four segments of the k-space data shown in FIG. 9A, assuming that the proton density source image p remains consistent across four segments, as shown in Equation 6:

$$u_{j,k}(x, y) = \sum_{r=0}^{3} S_j\left(x, y + \frac{r \times FOV_y}{4}\right) p\left(x, y + \frac{r \times FOV_y}{4}\right) e^{i2\pi \frac{k}{4}} \quad (6)$$

where $u_{j,k}$ represents aliased signal detected by the j-th coil in the k-th segment (k=1 to 4), and the phase term $$\exp\left(i2\pi \frac{k}{4}\right)$$

reflects the relative k-space trajectory shift among four segments. It can be seen that the proton density source signals in pixels p(x,y+r×FOV$_y$/4) (with r=0 to 3) can be jointly calculated from full k-space data through matrix inversion. As compared with a direct 2D Fourier transform of the full k-space data, the image reconstruction through solving Equation 6 imposes constraints during the reconstruction so that the reconstructed full-FOV image corresponds to a solution with the shortest Euclidean distance from data in all four segments, even in the presence of subtle inconsistencies across four segments in FIG. 9A. This constrained reconstruction algorithm will be useful for suppressing residual artifacts in images produced by the previously described k-t-bootstrapping module.

It should be noted that the conventional SENSE algorithm has a major limitation that the number of coils should be greater than the acceleration factor (4 in the example). In contrast, the constrained reconstruction based on solving Equation 6 is designed for processing full k-space data, and is thus applicable even when the number of coils is smaller than the number of segments. For example, for a 4-segment data set obtained with a 3-channel coil, the matrix inversion of Equation 6 solves 4 unknowns from 12 equations.

Challenges in Performing Constrained Reconstruction of Irregularly Sampled Cartesian or Non-Cartesian k-Space Data Equation 6 can be generalized to a matrix form, so that the concept of constrained reconstruction can be applied to k-space data obtained with either regularly or irregularly sub-sampling patterns in Cartesian k-space (e.g., as shown in FIGS. 9A and 9E, respectively). Generally, the constrained reconstruction of full-FOV image (of matrix size N×N) from multiple segments (1 to $N_S$) of sub-sampled Cartesian k-space data can be achieved by solving Equation 7.

$$u = ESp \tag{7}$$

where u is a vector of length $N^2$ containing the complex signals obtained from all segments and all coils (1 to $N_C$); p is a vector of length $N^2$ denoting the pixel-wise complex values of the un-aliased full FOV image to be reconstructed; S is a matrix of size $N^2N_C \times N^2$ describing the coil sensitivity profiles; and E is a matrix of size $N^2 \times N^2N_C$ illustrating the PSF corresponding to the chosen sampling pattern.

For segmented MRI data comprising multiple segments of regularly sub-sampled k-space data (e.g., solid and dashed ky lines in FIG. 9A), the corresponding PSF are a set of sharp peaks (FIG. 9B). In this case, E in Equation 7 contains the phase weighting of a relatively simple form (e.g., as illustrated by FIGS. 9C and 9D), and many of the matrix elements are zeros. Therefore, Equation 7 can be decomposed into multiple equations of a small matrix size (e.g., Equation 6) that can be solved with matrix inversion. However, as will be described in the Methods section, the sampling patterns of abdominal MRI may not always be as regular as that shown in FIG. 9A. When a more complicated sampling pattern is chosen (e.g., FIG. 9E), the corresponding PSF are no longer a set of sharp peaks (e.g., FIG. 9F). In this case, Equation 7 of a very large matrix size cannot be decomposed into multiple equations, and the matrix inversion based constrained reconstruction would be numerically challenging and computationally expensive. Similarly, the constrained reconstruction for data obtained with non-Cartesian sampling patterns may not be easily achievable with matrix inversion.

FIG. 9A illustrates an example of regular sub-sampling in k-space (usually achieved with 4-shot segmented MRI). FIG. 9B shows PSF corresponding to the first segment of FIG. 9A. FIG. 9C shows true (unaliased) image-domain signals. FIG. 9D illustrates an aliased image-domain signal resulting from the k-space undersampling (e.g., the first segment only of FIG. 9A) with the aliasing pattern predictable by the PSF. FIG. 9E shows an example of irregular sub-sampling in k-space. FIG. 9F shows a complicated PSF corresponding to the first segment of FIG. 9E.

Constrained Reconstruction Based on POCSMUSE

A POCS algorithm can be used to perform constrained reconstruction of irregularly sampled Cartesian or non-Cartesian k-space data. The POCS algorithm has been successfully used in various MRI applications. For example, Samsonov et al. have integrated POCS and SENSE into a framework, termed POCSENSE (18), to perform parallel MRI reconstruction for irregularly under-sampled k-space data. POCS and multiplexed sensitivity encoding of full k-space data (with its simplest form shown in Equation 6) can be integrated into a framework that can perform constrained reconstruction of full k-space data comprising multiple segments of irregularly sub-sampled data.

Figure 10:
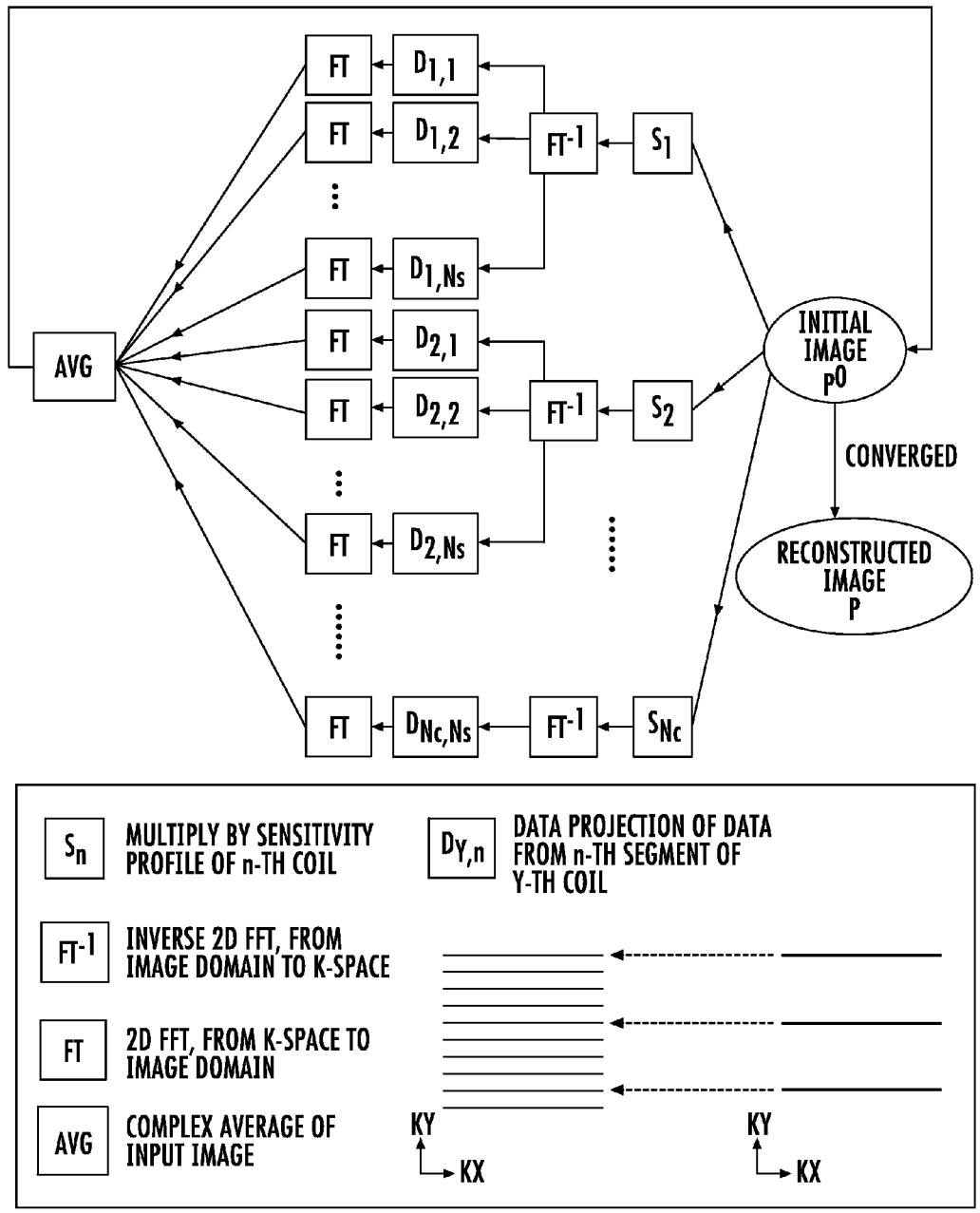
FIG. 10 is a schematic diagram of an exemplary POCSMUSE implementation according to embodiments of the present invention.

Exemplary constrained reconstruction framework is schematically illustrated in FIG. 10. The reconstruction can comprise the following steps. Step 1: An initial estimate or guess of proton density source image $P^i$ (i=0 at first iteration) can be used as the input or a default estimate can automatically be generated, which is then multiplied with the sensitivity profiles of coils $S_\gamma$ ($\gamma=1 \sim N_c$). Step 2: Images (of all coils) generated by step 1 can be transformed (with inverse 2D Fourier transform) to k-space signals $D_{\gamma,n}^i$ which are then projected to $D_{\gamma,n}^i$ (n=1~$N_S$). As shown in FIG. 10, the data projection from $D_\gamma^i$ to $D_{\gamma,n}^i U_{\gamma,n}^i$ can be achieved by replacing certain $k_y$ lines of the calculated $D_\gamma^i$ signals with the experimentally acquired signals. Step 3: The projected k-space signals $D_{\gamma,n}^i$ are transformed (with 2D Fourier transform) to image-domain complex signals $P_{\gamma,n}^i$, which are then averaged to generate a proton density source image $P^{i+1}$ for the subsequent iteration, as shown in Equation 8.

$$P^{i+1} = \sum_{\gamma=1}^{N_C} \sum_{n=1}^{N_S} \alpha_{\gamma,n} P_{\gamma,n}^i \tag{8}$$

$$\alpha_{\gamma,n} = \frac{S_\gamma^*}{\sum_{\gamma=1}^{N_C} \sum_{n=1}^{N_S} S_\gamma} \tag{9}$$

and $S_\gamma^*$ is the complex conjugate of the sensitivity profiles. Step 4: The iterative procedures described above are repeated until the proton density source image converges, i.e., when the absolute variation of an iteration (i.e., $e_{i+1}$ in Equation 10) falls below a predefined tolerance.

$$e_{i+1} = \frac{\| P^{i+1} - P^i \|}{\| P^i \|} \tag{10}$$

This constrained reconstruction that integrates POCS and multiple sensitivity encoding (MUSE) is termed POCSMUSE. It should be pointed that the current POCSMUSE framework (FIG. 10) is different from the MUSE procedure that reduces aliasing artifacts in segmented EPI based diffusion-weighted imaging (DWI) (19) in several ways. First, since the image-domain phase values are highly inconsistent across multiple segments of segmented DWI, in the previous implementation of MUSE-DWI, the SENSE method was used to estimate the shot-to-shot phase variations before calculating the proton density source images jointly from all segments. In contrast, for abdominal MRI based on FSE (or even gradient-echo imaging with short echo time), the phase variations across multiple segments are insignificant, and thus an initial SENSE-based estimation of the proton density source image from each of the segments is not needed in the current POCSMUSE framework. Second, in the previous MUSE-DWI method, the number of EPI segments could not be larger than the number of coil receive elements, since an initial SENSE estimation is required. In contrast, the current POCSMUSE method can be applied to segmented MRI with a number of segments greater than the number of coil receive elements (see last paragraph of subsection: SENSE reconstruction of undersampled data vs. constrained reconstruction of fully sampled data). Third, the previous MUSE-DWI method is typically applicable only to segmented EPI with regular k-space sub-sampling patterns (e.g., FIG. 9A). In contrast, the current POCSMUSE framework is more generally applicable to irregular data sampling in either Cartesian or non-Cartesian k-space.

In summary, the ReKAM technique consists of one acquisition module and can include two reconstruction modules. The ReKAM method is designed to eliminate motion-related artifacts in free-breathing abdominal MRI. It is expected that the ReKAM framework will be compatible with different abdominal MRI pulse sequences, including those with non-Cartesian trajectories.

Methods

The developed free-breathing ReKAM technique was evaluated with human MRI scans using a 3 Tesla system (General Electric, Waukesha Wis., USA) equipped with an 8-channel receiver coil. Data were acquired from three volunteers using a FSE sequence with the following parameters: TR=3750 ms, TE=100 ms, slice thickness=8 mm, number of slices=7 (subject #1) or 14 (subjects #2 and #3), FOV=40 cm×32 cm (subject #1) or 40 cm×40 cm (subjects #2 and #3), echo train length=16, and in-plane matrix size=320×206 (subject #1) or 256×256 (subjects #2 and #3). The number of segments were 14 for the 320×206 data set and 16 for the 256×256 data sets, respectively. Note that these segmented FSE k-space data were not regularly sampled (as in FIG. 9A). The irregular sampling patterns were chosen automatically by the manufacturer-provided FSE sequence, to accommodate the chosen parameters. Table 1 lists the ky lines obtained from each FSE segment in our experiments.

TABLE 1

K-y data for Each Segment

| Segment index | $K_y$ lines obtained for each segment | | | |
|---|---|---|---|---|
| | ETL = 14 | | ETL = 16 | |
| 1 | 1, 8, 15, . . . , 78, | 197, 204 | 1, 9, 17, . . . , 97, | 233, 241, 249 |
| 2 | 2, 9, 16, . . . , 72, | 191, 198, 205 | 2, 10, 18, . . . , 98, | 234, 242, 250 |
| 3 | 3, 10, 17, . . . , 73, | 192, 199, 206 | 3, 11, 19, . . . , 99, | 235, 243, 251 |
| 4 | 4, 11, 18, . . . , 74, | 193, 200 | 4, 12, 20, . . . , 100, | 236, 244, 252 |
| 5 | 5, 12, 19, . . . , 75, | 194, 201 | 5, 13, 21, . . . , 93, | 229, 237, 245, 253 |
| 6 | 6, 13, 20, . . . , 76, | 195, 202 | 6, 14, 22, . . . , 94, | 230, 238, 246, 254 |
| 7 | 7, 14, 21, . . . , 77, | 196, 203 | 7, 15, 23, . . . , 95, | 231, 239, 247, 255 |
| 8 | — | 79, 86, 93, . . . , 184 | 8, 16, 24, . . . , 96, | 232, 240, 248, 256 |
| 9 | — | 80, 87, 94, . . . , 185 | — | 101, 109, 117, . . . , 221 |
| 10 | — | 81, 88, 95, . . . , 186 | — | 102, 110, 118, . . . , 222 |
| 11 | — | 82, 89, 96, . . . , 187 | — | 103, 111, 119, . . . , 223 |
| 12 | — | 83, 90, 97, . . . , 188 | — | 104, 112, 120, . . . , 224 |
| 13 | — | 84, 91, 98, . . . , 189 | — | 105, 113, 121, . . . , 225 |
| 14 | — | 85, 92, 99, . . . , 190 | — | 106, 114, 122, . . . , 226 |
| 15 | — | — | — | 107, 115, 123, . . . , 227 |
| 16 | — | — | — | 108, 116, 124, . . . , 228 |

Five repetitions of full k-space free-breathing FSE data were acquired from each volunteer to evaluate the performance of the ReKAM method. The scan time of free-breathing FSE was 262.5 sec for 5 runs of 320×206 data, and 300 sec for 5 runs of 256×256 data. An additional set of FSE data was acquired while the subjects held their breath (52.5 sec for the 320×206 data set; 60 sec for the 256×256 data set) as a comparison. For each volunteer, the image reconstruction and analysis are described below:

1. Five sets of free-breathing FSE data were processed with the following procedures. First, the bootstrapping procedure was used to identify an image with the minimal artifact level in background ROIs (indicated by rectangles in FIG. 11A). Specifically, the bootstrapping module was performed using either the original k-space data (longer computation time) or only the central 64×64 portion of the k-space data (shorter computation time). In either case, the optimal k-t-data regrouping strategy was identified, and the full k-space data were recombined accordingly to produce an image with low artifact level. Second, the re-combined k-space data set then underwent the POCSMUSE reconstruction module to further reduce the residual artifact. Specifically, the initial guess of the proton density source image (i.e., $P^0$ in FIG. 10) was a 2D matrix of all zeros, and the convergence threshold was 0.01 (Equation 10).

2. The performance of ReKAM was quantitatively evaluated by measuring the ghost-to-signal ratio (GSR) of uncorrected free-breathing images and ReKAM-produced free-breathing images. Specifically, the ghost artifact level was measured from the background ROIs shown, and the parent signal level was measured from regions with lower intensity variation (indicated by ROIs in kidneys: FIG. 11A). The GSR values of breath-holding FSE data were also measured.

3. The signal-to-noise ratio (SNR) in uncorrected free-breathing FSE data, ReKAM-produced free-breathing data, and breath-holding FSE data were measured and compared. Specifically, the SNR value was measured by the ratio of the mean signal intensity to the standard deviation of signals within manually chosen ROIs (in kidneys: FIG. 11A). To further quantify the SNR penalty directly associated with the POCSMUSE module, the POCSMUSE algorithm was applied to a single breath-holding FSE data set, and the SNR values in images before and after applying the POCSMUSE algorithm were compared.

4. To further investigate the dependence of ReKAM-produced image quality on the number of repeated scans, the ReKAM reconstruction framework was applied to subsets of the acquired data (i.e., n out of 5 repetitions; with 2≤n≤5). For a fixed number of subsets, the ReKAM performance was evaluated, in terms of the GSR, using all possible combinations. For example, for two repeated scans, the ReKAM performance was evaluated using 10 (i.e., $C_2^5$) different ways of selecting 2 out 5 acquired data sets.

5. The k-t-bootstrapping module was implemented with C++, and the POCSMUSE module was implemented with Matlab. Image reconstruction and data analyses were performed in a Linux computer equipped with an Intel Xeon CPU (2.53 GHz) and 20 GB memory.

Results

Reconstructed images of three selected slices from one of the subjects (subject #1) are shown in FIGS. 11A-11C. Free-breathing and breath-holding images reconstructed with 2D Fourier transform, without any artifact correction, are shown in the set of image slices under FIGS. 11A and 11B, respectively. As expected, the free-breathing images (FIG. 11A) are corrupted by motion artifacts. It can be seen that, although the motion-related artifacts are greatly reduced by breath-holding, the acquired images are still affected by minor residual artifacts (arrows in FIG. 11B) likely resulting from involuntary movement of internal organs. FIG. 11C shows high-quality images reconstructed from the acquired free-breathing data (5 runs) using the ReKAM technique. The artifact level and anatomic resolvability in ReKAM-produced images are comparable to those in the breath-holding images. The ReKAM-produced free-breathing images from subjects #2 and #3 have similar quality (data not shown). However, subjects #2 and #3 could not hold their breath well throughout the breath-hold scans. Note that the final images reconstructed by 1) applying both k-t-bootstrapping and POCSMUSE modules to full k-space data, and 2) applying k-t-bootstrapping module to the central 64×64 k-space data and POCSMUSE module to full k-space data are identical.

FIG. 11A shows the uncorrected free-breathing data have significant motion-related artifacts (with GSR>11%); FIG. 11B shows that breath-holding data have higher image quality and lower artifact level (with GSR<9%); and FIG. 11C shows that free-breathing data reconstructed by the ReKAM method have high quality and the lowest artifact level (with GSR<6.5%).

The mean GSR value of all slices in the reconstructed images was measured from each subject. For subject 1, the mean GSR values of 1) uncorrected free-breathing images, 2) breath-holding images, 3) free-breathing images processed with only the k-t-bootstrapping module, and 4) ReKAM-reconstructed free-breathing images (i.e., processed with both k-t-bootstrapping and POCSMUSE modules) were 0.133, 0.098, 0.100 and 0.071, respectively. For subject 2, the corresponding mean GSR values were 0.151, 0.101, 0.114 and 0.0743. For subject 3, the corresponding mean GSR values were 0.155, 0.12, 0.134 and 0.091, respectively. Mean and standard deviations of GSR values across the three subjects were 0.146±0.012, 0.106±0.012, 0.116±0.017, and 0.079±0.011. These data show that the developed ReKAM method can be used to suppress the artifacts in uncorrected free-breathing images by approximately 46%. In addition, these GSR measures show that the POCSMUSE module is helpful in reducing the residual artifact in free-breathing images processed only by the k-t-bootstrapping module. Furthermore, it can be seen that the GSR values of the ReKAM produced images are even lower than those of breath-holding images, demonstrating the effectiveness of the developed ReKAM technique.

The SNR values of the reconstructed images in the region of the kidneys were also measured from each subject. For subject 1, the mean SNR values for 1) uncorrected free-breathing images, 2) breath-holding images, and 3) ReKAM-reconstructed free-breathing images were 8.05, 9.95 and 8.36, respectively. For subject 2, the corresponding mean SNR values were 11.67, 10.73 and 11.1. For subject 3, the corresponding mean SNR values were 11.21, 9.73 and 10.89. Mean and standard deviations of SNR across the three subjects were 10.31±1.97, 10.14±0.53, and 10.12±1.52. These quantitative measures show that ReKAM technique can produce high-quality free-breathing images with SNR comparable to that of breath-holding MRI.

In order to quantify the potential SNR penalty directly associated with the POCSMUSE module, the SNR values in breath-holding images was compared with and without applying the POCSMUSE-based constrained reconstruction. For subject 1, the SNR values for breath-holding images with and without POCSMUSE constrained reconstruction were 9.92 and 9.95 respectively. The corresponding SNR values for subject 2 were 10.74 (with POCSMUSE) and 10.73 (without POCSMUSE). The corresponding SNR values for subject 3 were 9.76 (with POCSMUSE) and 9.73 (without POCSMUSE). Mean and standard deviations of SNR across the three subjects were 10.33±0.60 and 10.34±0.55. These data suggest that the POCSMUSE constrained reconstruction does not alter the SNR level significantly.

Figure 12:
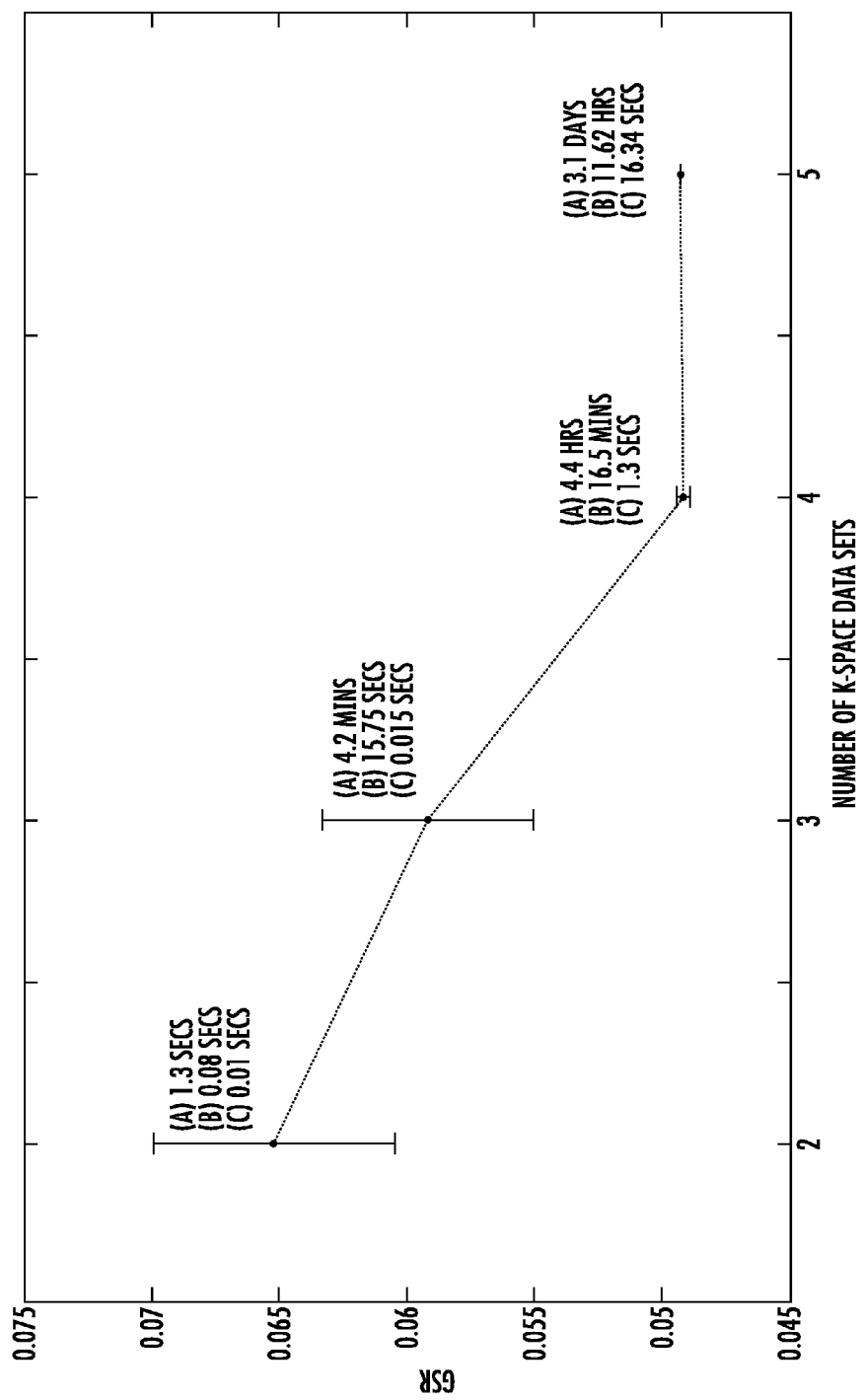
FIG. 12 is a graph of the mean and standard deviation of GSR in ReKAM-produced images versus different numbers of data repetition (different numbers of k-space data sets). The computational time of the ReKAM method are reported for (a) bootstrapping based on the full Fourier k-space data (256×256), (b) bootstrapping based on the central k-space data (64×64), and (c) full-Fourier bootstrapping after rejecting 50% of the data time points (e.g., corresponding to different respiratory phases based on either navigator-echoes or belly-belt based estimation).

In FIG. 12, the dependence of the ReKAM performance (in terms of the GSR in a selected slice) on the number of repeated scans is shown. It can be seen that, for FSE imaging with chosen parameters, GSR values fall as the number of repeated scans rises, up to 4 repeated scans. ReKAM performance does not improve by further increasing the number of repeated scans to 5.

In FIG. 12, the ReKAM computational time for two data processing pipelines is also shown: (a) applying both k-t-bootstrapping and POCSMUSE modules to full k-space data, and (b) applying k-t-bootstrapping module to low k-space data and POCSMUSE module to full k-space data. It can be seen that the reconstruction time can be significantly reduced if the k-t-bootstrapping module is applied to low k-space data instead of full k-space data (e.g., 16.5 min instead of 4.4 hours for 4 repeated scans). In the Discussion section other possible approaches to further reduce the computation time (e.g., to 1.3 sec for 4 repeated scans) is provided.

FIG. 12 shows the mean and standard deviation of GSR in ReKAM-produced images corresponding to different numbers of data repetition. The computational time of the ReKAM method are reported for (a) bootstrapping based on the full Fourier k-space data (256×256), (b) bootstrapping based on the central k-space data (64×64), and (c) full-Fourier bootstrapping after rejecting 50% of the data time points (e.g., corresponding to different respiratory phases based on either navigator-echoes or belly-belt based estimation).

Discussion

The developed ReKAM method has several strengths. First, since the ReKAM method is compatible with different MRI pulse sequences, requiring no or little sequence modification, it may be used as a core technique to reliably enable abdominal MRI with different clinically required or useful contrasts. Second, the POCSMUSE module included in the ReKAM pipeline can be a very general mathematical framework, capable of reconstructing images from either Cartesian or non-Cartesian k-space data. Third, the ReKAM method can produce high-quality abdominal MRI data without requiring the subjects to hold their breath and/or without relying on respiratory gating. Therefore, it is expected to be particularly useful for challenging subjects (e.g., seriously ill patients, children). Furthermore, the artifacts resulting from involuntary and nonlinear motion of internal organs may not be suppressed with either respiratory gating or breath holding (e.g., indicated by an arrow in FIG. 11B), and may be better removed with the ReKAM method (e.g., FIG. 11C), so the method may even improve image quality in patients who are capable of breath holding.

As illustrated by the experimental results, respiratory motion related artifacts can be reduced through k-t-data bootstrapping and POCSMUSE, without relying on navigator echoes or non-MRI measurement (e.g., belly-belt). It is worth noting that if the navigator echoes or any non-MRI measurement of respiratory cycles are available, they are compatible with the ReKAM method and can be used to significantly reduce the computational cost of the k-t-data bootstrapping. For example, even with a rough belly-belt based estimation of the respiratory cycles, one may easily exclude 50% of the data (corresponding to different respiratory phases) from the k-t-data bootstrapping, and the recomputation time for our 4-repetition full-Fourier bootstrapping can be reduced from 4.4 hours to 1.3 seconds (FIG. 12). Alternatively or additionally, the ReKAM computation time could also be substantially reduced by utilizing parallel computation on multiple CPU or general purpose GPU units.

In the bootstrapping module, an image with the lowest artifact level is identified based on the artifact energy level in background ROIs (FIG. 8C). This approach works well and reliably for data obtained with the segmented k-space sampling scheme (e.g., multi-shot segmented EPI; multi-shot FSE), where the intra-scan motion results in ghosting artifacts. On the other hand, the intra-scan subject motion during sequential k-space sampling scheme, e.g., in conventional T1-weighted spoiled gradient recalled (SPGR) imaging, results in blurring artifacts rather than ghosting artifacts. Since the blurring artifacts may not be easily detected with ROI-based measurement, modifying the acquisition order of T1-weighted SPGR from sequential sampling (e.g., 1, 2, 3 . . . 256) to segmented sampling (e.g., 1, 5, 9 . . . 253, 2, 6, 10 . . . ) may be useful so that the developed ReKAM framework can be directly applied to free-breathing T1-weighted SPGR imaging.

It may be convenient to use the data from each FSE segment as a unit for performing k-t-data regrouping (e.g., FIGS. 8A and 8B). For example, in 16-shot FSE imaging studies (Table 1), 16 ky lines acquired in each FSE segment were treated as a unit when performing k-t-data regrouping. However, it should be pointed out that the k-t-data regrouping scheme used in Reconstruction Module 1 is not required to match the segmented k-space sampling scheme used in data acquisition. For example, if there are significant intra-segment motions within each FSE segment (e.g., due to very high respiratory rates), one could further decompose those 16 ky lines acquired in the 16-shot FSE scans into two bootstrapping units (with the 1st to 8th ky lines as the first unit, and the 9th to 16th ky lines as the second unit) or even more units when performing the k-t-bootstrapping, to better suppress motion related artifacts (at the cost of greater computation time).

Although the developed ReKAM method has only been applied to free-breathing abdominal MRI, it should be useful for several other applications. For example, for neuro-imaging of Parkinson's patients with continual head tremors, one may acquire a series of images and then use the ReKAM modules to remove motion-related artifacts. In addition, it may be worthwhile to explore the feasibility of applying the ReKAM method to reduce motion-related artifacts in free-breathing cardiac cine imaging without (or with) gating.

In conclusion, the ReKAM framework provides high-quality and free-breathing abdominal MRI, and is compatible with various MRI pulse sequences. The developed k-t-data bootstrapping and POCSMUSE reconstruction modules can be generally applied to remove motion artifacts in Cartesian and non-Cartesian k-space data obtained with different pulse sequences. The ReKAM technique may prove valuable for clinical imaging of patients who cannot hold their breath for an extended period of time or have irregular respiratory rates.

Figure 13:
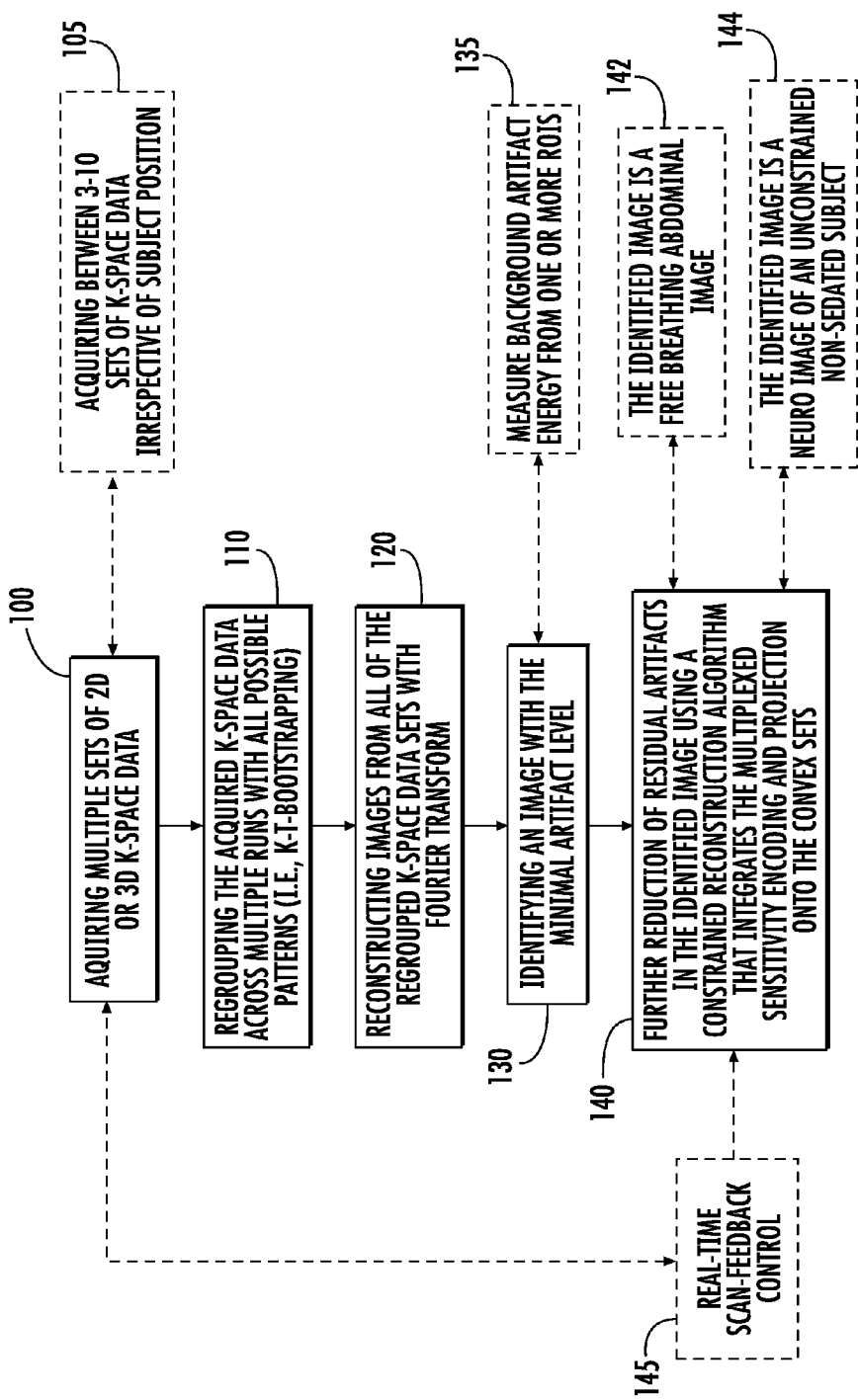
FIG. 13 is a flow chart of exemplary actions that can be performed to generate MRI images according to embodiments of the present invention.

FIG. 13 is a flow chart of exemplary steps that can be used to generate MRI images with reduced motion-induced motion artifacts and/or motion aliasing artifacts. Multiple sets of 2D or 3D k-space data are acquired (block 100). The acquired k-space data is regrouped across multiple runs with all possible patterns to carry out k-t bootstrapping (block 110). Images from the regrouped k-space data are reconstructed with Fourier transform (block 120). An image with a lowest artifact level is electronically, automatically identified (block 130). Further reduction of residual artifacts in the identified image can be carried out using a constrained reconstruction algorithm that integrates multiplexed sensitivity encoding and projection onto convex (data) sets (block 140).

Acquiring data can be carried out by acquiring between 3-10 sets of k-space data (typically 3-5, such as 4) irrespective of subject position (block 105).

Identification can be carried out by evaluating background artifact energy from one or more ROIs (block 135).

The identified images can be free breathing abdominal images (block 142).

The identified image can be a neuro (brain) image of an unconstrained or un-sedated patient subject to undesired head movement during the scan (block 144).

The identifying and/or further reduction of artifacts can be used to provide scan feedback to identify whether to continue to acquire k-t data sets or to stop the scanning (block 145).

Figure 14A:
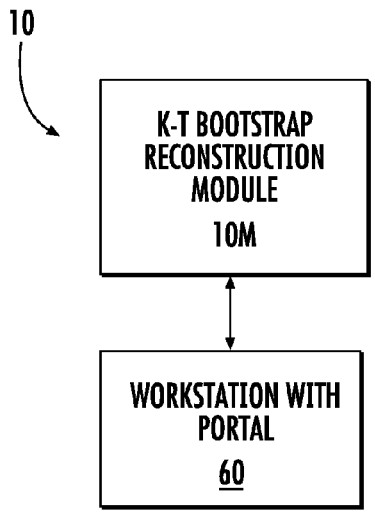
FIGS. 14A-14C are schematic illustrations of different systems that include or communicate with image processing circuits configured to carry out k-t space bootstrapping reconstruction to reduce artifact errors according to embodiments of the present invention.
Figure 14B:
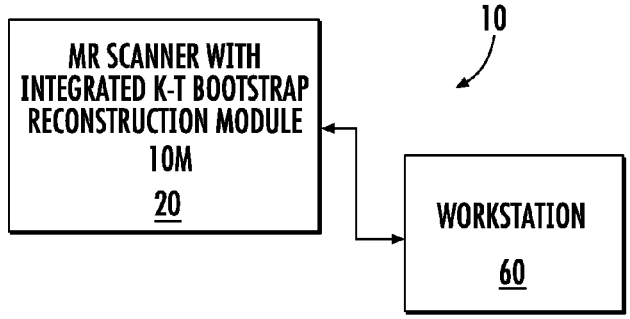
Figure 14C:
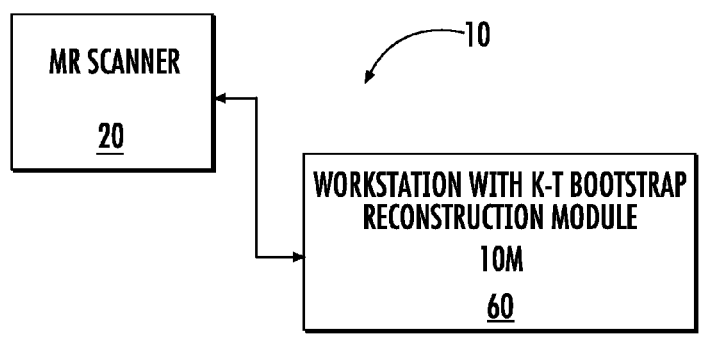

FIGS. 14A-14C illustrate exemplary image processing systems 10 with a bootstrapping reconstruction module or circuit 10M with or without the constrained reconstruction module.

FIG. 14A illustrates that the system 10 can include at least one workstation 60 that has a portal for accessing the module 10M. The module 10M can be held on a remote server accessible via a LAN, WAN or Internet. The workstation 60 can communicate with patient image data which may be held in a remote or local server, in the Scanner or other electronically accessible database or repository. The workstation 60 can include a display with a GUI (graphic user input) and the access portal. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 14B illustrates that the module 10M can be included in the MR Scanner 20 which can communicate with a workstation 60. The module 10M can be integrated into the control cabinet with image processing circuitry.

FIG. 14C illustrates that the module 10M can be integrated into one or more local or remote workstations 60 that communicates with the Scanner 20. Although not shown, parts of the module 10M can be held on both the Scanner 20 and one or more workstations 60, which can be remote or local.

Figure 15:
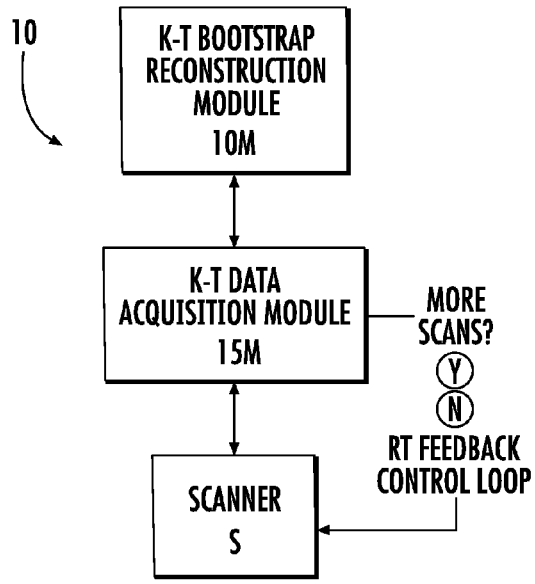
FIG. 15 is a schematic illustration of a control circuit for a scanner using a feedback circuit with k-t acquisition module according to embodiments of the present invention.

FIG. 15 illustrates that the image processing system 10 can include the k-t data bootstrapping module 10M and a k-t space data acquisition module 15M that is in communication with an MRI scanner S to provide a control feedback circuit to control the acquisition of k-t data based on when an image is reconstructed with a sufficiently low artifact background energy level.

Some or all of the module 10M (and/or 15M) (or one or more of the modules 449, 450, 451, FIG. 16) can be held on at least one server that can communicate with one or more Scanners 20. The at least one server can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Firewalls and suitable security protocols can be followed to exchange and/or analyze patient data.

Figure 16:
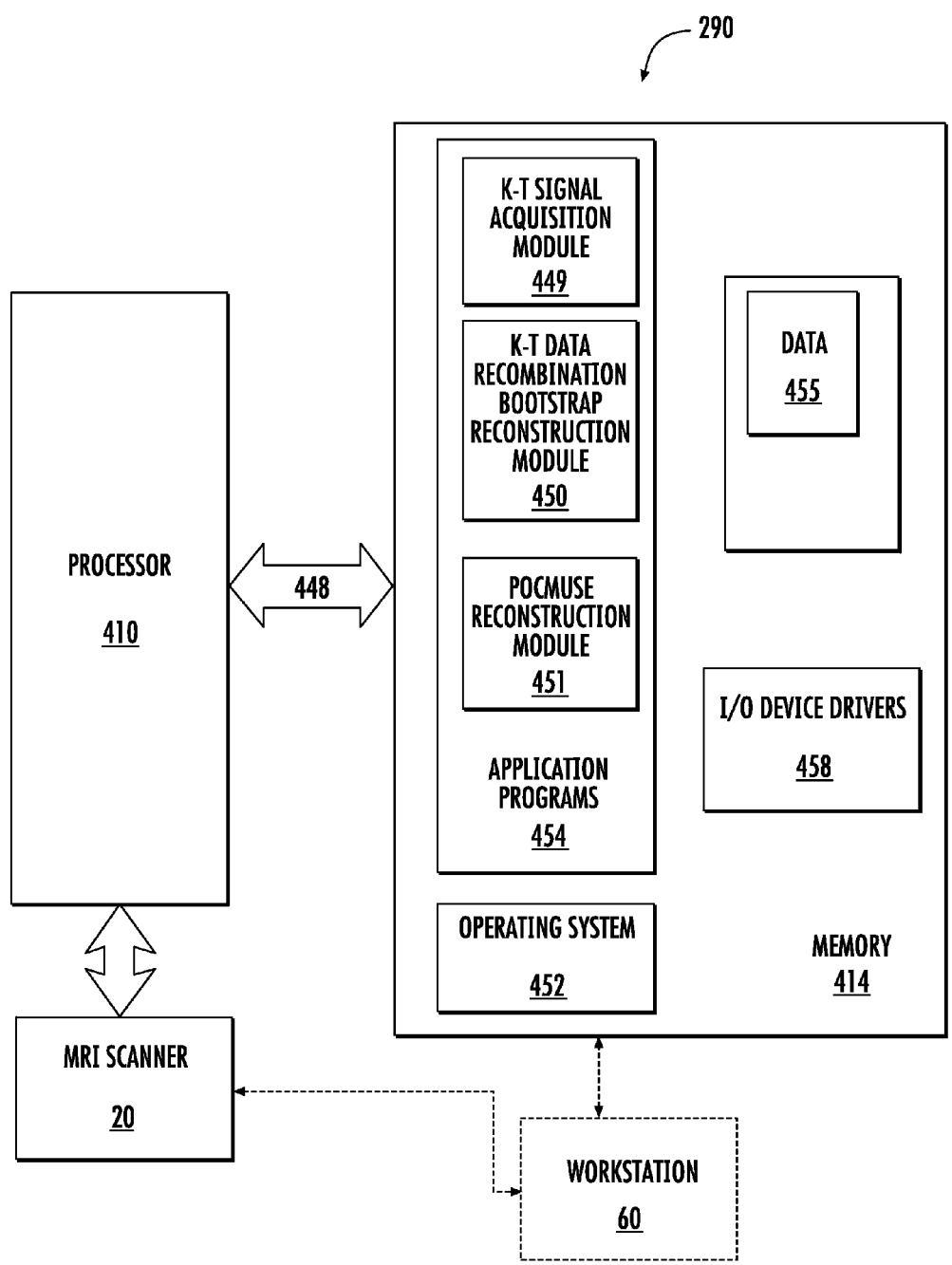
FIG. 16 is a schematic illustration of a data processing system according to embodiments of the present invention.

FIG. 16 is a schematic illustration of a circuit or data processing system 290. The system 290 can be used with any of the systems 10 and provide all or part of the module 10M and/r module 15M. The circuits and/or data processing systems 290 data processing systems may be incorporated in a digital signal processor in any suitable device or devices. As shown in FIG. 16, the processor 410 can communicate with an MRI scanner 20 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 16 illustrates that the memory 414 may include several categories of software and data used in the data processing system: the operating system 452; the application programs 454; the input/output (I/O) device drivers 448; and data 455. The data 455 can include 2-D and/or 3-D k-t space data patient-specific MRI image data.

FIG. 16 also illustrates the application programs 454 can include a k-t boot strap reconstruction Module 450, a POCMUSE reconstruction Module 451, and a signal acquisition Module 449.

The data processing system may be particularly suitable for imaging of the brain and/or free breathing abdominal or cardiac imaging.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 448 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 448, and other software programs that may reside in the memory 414.

While the present invention is illustrated, for example, with reference to the Module 450 being an application program in FIG. 16, as will be appreciated by those of skill in the art, other configurations may also be utilized while still benefiting from the teachings of the present invention. For example, one or more of the Modules 450, 451, 449 may also be incorporated into the operating system 452, the I/O device drivers 458 or other such logical division of the data processing system. Thus, the present invention should not be construed as limited to the configuration of FIG. 16 which is intended to encompass any configuration capable of carrying out the operations described herein. Further, one or more of Module 450, Module 451 and/or Module 449 can communicate with or be incorporated totally or partially in other components, such as an MRI scanner 20, interface/gateway or workstation 60.

The I/O data port can be used to transfer information between the data processing system, the workstation, the MRI scanner, the interface/gateway and another computer system or a network (e.g., the Internet) or to other devices or circuits controlled by the processor. These components may be conventional components such as those used in many conventional data processing systems, which may be configured in accordance with the present invention to operate as described herein.

REFERENCES

1. Ehman R L, Felmlee J P. Adaptive technique for high-definition M R imaging of moving structures. Radiology 1989; 173(1):255-263.
2. Vasanawala S S, Iwadate Y, Church D G, Herfkens R J, Brau A C. Navigated abdominal T1-W MRI permits free-breathing image acquisition with less motion artifact. Pediatric radiology 2010; 40(3):340-344.
3. Pipe J G. Motion correction with PROPELLER MRI: application to head motion and free-breathing cardiac imaging. Magnetic resonance in medicine: official journal of the Society of Magnetic Resonance in Medicine/Society of Magnetic Resonance in Medicine 1999; 42(5): 963-969.

4. Forbes K P, Pipe J O, Bird C R, Heiserman J E. PROPELLER MRI: clinical testing of a novel technique for quantification and compensation of head motion. Journal of magnetic resonance imaging: JMRI 2001; 14(3):215-222.
5. Rohlfing T, Maurer C R, Jr., O'Dell W G, Zhong J. Modeling liver motion and deformation during the respiratory cycle using intensity-based nonrigid registration of gated M R images. Medical physics 2004; 31(3):427-432.
6. Odille F, Vuissoz P A, Marie P Y, Felblinger J. Generalized reconstruction by inversion of coupled systems (GRICS) applied to free-breathing MRI. Magnetic resonance in medicine: official journal of the Society of Magnetic Resonance in Medicine/Society of Magnetic Resonance in Medicine 2008; 60(1):146-157.
7. White M J, Hawkes D J, Melbourne A, Collins D J, Coolens C, Hawkins M, Leach M O, Atkinson D. Motion artifact correction in free-breathing abdominal MRI using overlapping partial samples to recover image deformations. Magnetic resonance in medicine: official journal of the Society of Magnetic Resonance in Medicine/Society of Magnetic Resonance in Medicine 2009; 62(2):440-449.
8. Wachtel R E, Dexter F, Dow A J. Growth rates in pediatric diagnostic imaging and sedation. Anesthesia and analgesia 2009; 108(5):1616-1621.
9. Katz R C, Wilson L, Frazer N. Anxiety and its determinants in patients undergoing magnetic resonance imaging. Journal of behavior therapy and experimental psychiatry 1994; 25(2):131-134.
10. Eshed I, Althoff C E, Hamm B, Hermann K G. Claustrophobia and premature termination of magnetic resonance imaging examinations. Journal of magnetic resonance imaging: JMRI 2007; 26(2):401-404.
11. Lukins R, Davan I G, Drummond P D. A cognitive behavioural approach to preventing anxiety during magnetic resonance imaging. Journal of behavior therapy and experimental psychiatry 1997; 28(2):97-104.
12. Katznelson R, Djaiani G N, Minkovich L, Fedorko L, Carroll J, Borger M A, Cusimano R J, Karski J. Prevalence of claustrophobia and magnetic resonance imaging after coronary artery bypass graft surgery. Neuropsychiatric disease and treatment 2008; 4(2):487-493.
13. Oshio K, Feinberg D A. GRASE (Gradient- and spin-echo) imaging: a novel fast MRI technique. Magnetic resonance in medicine: official journal of the Society of Magnetic Resonance in Medicine/Society of Magnetic Resonance in Medicine 1991; 20(2):344-349.
14. Reddy B S, Chatterji B N. An FFT-based technique for translation, rotation, and scale-invariant image registration. IEEE transactions on image processing: a publication of the IEEE Signal Processing Society 1996; 5(8):1266-1271.
15. Besl P J, McKay N D. Method for registration of 3-D shapes. 1992. p 586-606.
16. Pruessmann K P, Weiger M, Scheidegger M B, Boesiger P. SENSE: sensitivity encoding for fast MRI. Magnetic resonance in medicine: official journal of the Society of Magnetic Resonance in Medicine/Society of Magnetic Resonance in Medicine 1999; 42(5):952-962.
17. Buehrer M, Pruessmann K P, Boesiger P, Kozerke S. Array compression for MRI with large coil arrays. Magnetic resonance in medicine: official journal of the Society of Magnetic Resonance in Medicine/Society of Magnetic Resonance in Medicine 2007; 57(6):1131-1139.
18. Samsonov A A, Kholmovski E G, Parker D L, Johnson C R. POCSENSE: POCS-based reconstruction for sensitivity encoded magnetic resonance imaging. Magnetic resonance in medicine: official journal of the Society of Magnetic Resonance in Medicine/Society of Magnetic Resonance in Medicine 2004; 52(6):1397-1406.
19. Chen N K, Guidon A, Chang H C, Song A W. A robust multi-shot scan strategy for high-resolution diffusion weighted MRI enabled by multiplexed sensitivity-encoding (MUSE). Neurolmage 2013; 72:41-47.

Any patents or publications mentioned in this specification are indicative of the levels of those skilled in the art to which the invention pertains. These patents and publications are herein incorporated by reference to the same extent as if each individual publication was specifically and individually indicated to be incorporated by reference at the location noted by the citation referencing the document. In case of conflict, the present specification, including definitions, will control.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:
1. A method of processing MRI image data to reduce or eliminate motion-related artifacts in MRI images, comprising:
electronically repeatedly acquiring multiple sets of 2D or 3D k-space data of a target region of a subject during different respiratory phases of free breathing using at least one MRI pulse sequence;
electronically applying a bootstrapping procedure which assembles different sub-sets of k-space data across multiple full k-space scans using different assembly patterns, wherein the different assembly patterns comprise a first assembly pattern of ky lines at a first scan time, a different second assembly pattern of ky lines at a second scan time and a third different assembly pattern of ky lines at a third scan time to produce different assembled images from the different subsets of the acquired k-space data; then
electronically measuring one or more motion induced artifact in each of the assembled images produced by the bootstrapping procedure, wherein the measured one or more motion induced artifact comprises measuring one or more of an aliasing artifact, blurring or entropy; and
electronically identifying one of the different assembled images with a lowest level of the measured one or more measured motion induced artifact as an image with a minimal motion-related artifact level,
wherein the acquiring, applying, measuring and identifying are carried out using at least one processor.

2. The method of claim 1, further comprising, after the electronic identification of the one of the assembled images as the image with the minimal motion-related artifact, programmatically using radiofrequency (RF) coil sensitivity profiles to perform a constrained image reconstruction from the assembled image to further remove residual artifact in the identified image to thereby generate an MRI image with reduced residual motion-related artifacts.

3. The method of claim 1, wherein the at least one MRI pulse sequence has regular segmented k-space sampling in Cartesian coordinates.

4. The method of claim 3, wherein the at least one MRI pulse sequence comprises at least one of segmented echo-planar imaging (EPI), segmented fast spin-echo imaging (FSE), segmented gradient-echo and spin-echo (GRASE) imaging, in which all segments have the same number of ky lines and the same inter-ky distance in 2D imaging or the same number of kykzplanes and the same inter-ky distance in 3D imaging.

5. The method of claim 1, wherein the at least one MRI pulse sequence comprises an irregular segmented k-space sampling in either Cartesian or non-Cartesian coordinates.

6. The method of claim 5, wherein the at least one MRI pulse sequence comprises segmented fast spin-echo imaging (FSE) in which all segments have different numbers of ky lines and different inter-ky distances in 2D imaging or different numbers of ky-kz-planes and different inter-kz distances in 3D imaging.

7. The method of claim 1, wherein the at least one MRI pulse sequence is configured to sample k-space in a non-sequential segmented manner.

8. The method of claim 7, wherein the at least one MRI pulse sequence includes either or both (a) modified spoiled gradient-echo imaging (SPGR) and (b) modified magnetization prepared rapid gradient echo (MP-RAGE) sequences, in which k-space sampling trajectories are modified from a sequential manner to a segmented manner.

9. The method of claim 1, wherein the at least one MRI pulse sequence is configured to sample k-space in a sequential manner.

10. The method of claim 9, wherein the at least one MRI pulse sequence includes SPGR and/or MP-RAGE imaging sequences.

11. A method for generating high-resolution, free-breathing abdomen MRI images, comprising:
    electronically acquiring multiple sets of 2D or 3D k-space data of abdominal MRI, over different respiratory phases of a free breathing subject using at least one MRI pulse sequence;
    electronically applying a bootstrapping procedure which assembles different subsets of k-space data across multiple full-k-space scans using different possible assembling patterns to produce assembled images from acquired subsets of 2D or 3D k-space data; then
    electronically measuring one or more motion-induced artifact in each of the assembled images produced by the bootstrapping procedure; and
    electronically identifying an image with a minimal motion-related artifact level from the assembled images produced by the bootstrapping procedure based on the measurement.

12. The method of claim 11, further comprising, after the electronic identification, programmatically using RF coil sensitivity profiles to perform a constrained image reconstruction from the identified image to further remove residual artifact in the identified image to thereby generate an MRI image with reduced residual motion-related artifacts.

13. The method of claim 1, wherein the electronically applying the bootstrapping procedure comprises:
    regrouping the acquired k-space data across repeated runs irrespective of subject position during a respective acquiring run and using, for the different assembly patterns, (i) all possible or selected patterns of k-t-space regrouping patterns of all the k-t space data or (ii) all possible or selected patterns of a defined center portion of the k-t space data; to reconstruct images from all the assembled k-space data with Fourier transform.

14. The method of claim 1, wherein the electronic measurement to identify the image with the minimal artifact level is carried out by at least one of the following:
    (i) electronically measuring a ghost energy level in defined regions of interest (ROI) located in a background area provided that a low ghost energy level indicates a low artifact level in images obtained with non-sequential MRI pulse sequences used for the acquiring step;
    (ii) electronically measuring an entropy level of a respective whole assembled image of each of the different assembled images as the measured entropy provided that a low entropy level indicates a low aliasing artifact level in images obtained with non-sequential segmented MRI pulse sequences used for the acquiring step; or
    (iii) electronically measuring a blurring level of a respective whole assembled image of each of the different assembled images as the measured blur provided that a low blurring level indicates a low artifact level in images obtained with sequential pulse sequences that are used for the acquiring step.

15. The method of claim 2, wherein the RF coil sensitivity profiles are of the RF coils used to acquire the k-space data to solve a full field-of-view (FOV) proton density source image without aliasing artifacts, jointly from all or at least two parts of k-space data segments, thereby assuming that the proton density source image remains consistent across multiple k-space data segments.

16. The method of claim 15, wherein the full-FOV proton density source image is reconstructed from the acquired k-space data and the known coil sensitivity profiles using at least one of the following:
    a direct matrix inversion for MRI data obtained with regular k-space sampling and typical k-space segment trajectories in Cartesian coordinates; or
    projection onto convex sets (POCS) for MRI data obtained with irregular k-space sampling and irregular k-space segment trajectories in either Cartesian or non-Cartesian coordinates.

17. The method of claim 2, wherein the known RF coil sensitivity profiles are of RF coils used to acquire the k-space data, and wherein the constrained reconstruction is carried out by:
    electronically estimating a first proton density source image;
    electronically calculating representations of the estimated proton density source image in all of the RF coils;
    electronically projecting experimentally acquired data to the estimated images in the corresponding RF coils to generate projected images;
    electronically integrating the projected images from all coils to form a new estimated proton density source image; and iteratively repeating the calculating, projecting and integrating steps until a new estimated proton density source image converges so that an absolute variation of an iteration falls below a predefined tolerance value.

18. The method of claim 17, wherein the projection is achieved by replacing certain $k_y$ lines of the k-space data of the estimated images with experimentally acquired signals.

19. The method of claim 1, wherein the bootstrapping procedure is carried out using one or more of the following to reduce computational demands:
(i) electronically performing the assembled images with different assembly patterns including the first assembly pattern at the first scan time, the second assembly pattern at the second scan time and the third assembly pattern at the third scan time of the bootstrapping procedure are carried out on only a central portion of the k-space data rather than full k-space data;
(ii) electronically using embedded navigator echoes to identify and exclude data points which do not correspond to a same motion state and/or subject position from the bootstrapping procedure;
(iii) electronically using non-MRI measures of patient position or movement and exclude data points which do not correspond to the same position from the bootstrapping procedure; or
(iv) electronically using a multi-core CPU and/or GPU to perform parallel computation of the bootstrapping procedure.

20. The method of claim 1, wherein a k-t-data regrouping scheme provided by the different assembly patterns used in the bootstrapping procedure is not required to match a segmented k-space sampling scheme used in data acquisition of the k-space data.

21. The method of claim 20, wherein the k-t data regrouping scheme provided by the different assembly patterns used in bootstrapping procedure can be carried out by one of more of the following:
a segmented k-space sampling scheme used in data acquisition; or
further decomposition of the ky lines acquired from each segment into two or more bootstrapping units.

22. The method of claim 1, wherein the acquired k-space data of the target region is one of abdominal MRI, cardiac MRI, neuro MRI or other anatomical regions susceptible to motion-related artifacts.

23. The method of claim 1, wherein the method is carried out using an image processing circuit comprising the at least one processor.

24. The method of claim 1, wherein the method is carried using an MRI image processing system comprising the at least one processor that is in communication with and/or at least partially on-board an MRI Scanner system.

25. The method of claim 1, wherein the method is carried using a data processing system with the at least one processor and comprising non-transitory computer readable storage medium having computer readable program code embodied in the medium, the computer-readable program code comprising computer readable program code configured to carry out the method.

26. An MRI image generation system with an image processing circuit comprising:
a k-t space data acquisition module; and
a bootstrapping procedure reconstruction module configured to regroup acquired k-space data from the k-t space data acquisition module across multiple subsets of 2D and/or 3D k-space data with all or selected possible assembly patterns of (i) an entire k space data matrix or (ii) only a center portion of the k space data matrix, to generate different assembled images with different motion-aliasing or induced artifact levels from respective regrouped k-space data sets, then identify a high quality image from the different generated images, wherein the identified high quality image is identified by one of the different assembled images having at least one of the following:
(i) a lowest ghost energy level in a defined region of interest (ROI) located in a background area;
(ii) a lowest entropy level; or
(iii) a lowest blurring level.

27. The system of claim 26, further comprising a constrained reconstruction module that uses RF coil sensitivity profiles to perform a constrained image reconstruction that integrates multiplexed sensitivity encoding and projection onto convex data sets and further adjusts artifact levels in the identified image from the bootstrapping procedure reconstruction module.

28. The system of claim 26, wherein the image processing circuit is in communication with and/or at least partially on-board an MR Scanner system.

29. The system of claim 27, wherein the constrained reconstruction module can be applied to both Cartesian and non-Cartesian MRI data obtained from free breathing fast-spin-echo cardiac and/or abdominal scans and/or free breathing cardiac and/or abdominal DWI scans.

30. The system of claim 26, wherein the data acquisition module employs between 4-6 scans to generate respective 4-6 2-D or 3-D k space data sets for use in the regrouped data subsets.

31. The method of claim 11, wherein the measuring of the one or more motion induced artifact comprises measuring one or more of an aliasing artifact, blurring or entropy.

* * * * *

UNITED STATES PATENT AND TRADEMARK OFFICE
CERTIFICATE OF CORRECTION

PATENT NO. : 10,317,499 B2
APPLICATION NO. : 14/769374
DATED : June 11, 2019
INVENTOR(S) : Chen et al.

Page 1 of 1

It is certified that error appears in the above-identified patent and that said Letters Patent is hereby corrected as shown below:

In the Specification

Column 18, Line 51: Please correct "(GRASS)" to read -- (GRASE) --

Column 22, Line 30: Please correct "$D_{y,n}^{i}$" to read -- $D_y^i$ --

In the Claims

Column 33, Line 19, Claim 4: Please correct "kykzplanes" to read -- ky-kz-planes --

Signed and Sealed this
First Day of October, 2019

Andrei Iancu
*Director of the United States Patent and Trademark Office*